US009195289B2

(12) United States Patent
Lee et al.

(10) Patent No.: US 9,195,289 B2
(45) Date of Patent: *Nov. 24, 2015

(54) TOUCH SCREEN INTERFACE AND INFRARED COMMUNICATION SYSTEM INTEGRATED INTO A BATTERY

(71) Applicant: Thoratec Corporation, Pleasanton, CA (US)

(72) Inventors: Eric Lee, Oakland, CA (US); Ethan Petersen, Oakland, CA (US); Joseph Stark, San Leandro, CA (US); Ian McCutcheon, Danville, CA (US); Steve Reichenbach, Pleasanton, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/455,843

(22) Filed: Aug. 8, 2014

(65) Prior Publication Data

US 2015/0022375 A1    Jan. 22, 2015

Related U.S. Application Data

(63) Continuation of application No. 13/894,284, filed on May 14, 2013, now Pat. No. 8,827,890.

(60) Provisional application No. 61/648,428, filed on May 17, 2012.

(51) Int. Cl.
*A61N 1/362* (2006.01)
*G06F 1/26* (2006.01)
(Continued)

(52) U.S. Cl.
CPC ............. *G06F 1/263* (2013.01); *A61M 1/1086* (2013.01); *A61M 1/122* (2014.02); *A61M 1/127* (2013.01); *G06F 1/3218* (2013.01); *G08C 23/04* (2013.01); *A61M 2205/3569* (2013.01); *A61M 2205/3592* (2013.01); *A61M 2205/505* (2013.01)

(58) Field of Classification Search
CPC .................... A61M 1/127; A61M 2205/3576; A61M 2205/3592; A61M 2205/3553; A61M 2205/3569; A61M 1/1086; A61M 1/10
See application file for complete search history.

(56) References Cited

U.S. PATENT DOCUMENTS

| 4,091,272 A | 5/1978 | Richter et al. |
| 4,151,407 A | 4/1979 | McBride et al. |

(Continued)

FOREIGN PATENT DOCUMENTS

WO    WO-2011081626    7/2011

OTHER PUBLICATIONS

PCT International Search Report and Written Opinion of the International Searching Authority for corresponding International Application No. PCT/US2013/041447, mailing date Aug. 14, 2013, 19 pages.

*Primary Examiner* — Robert N Wieland
(74) *Attorney, Agent, or Firm* — Blakely, Sokoloff, Taylor & Zafman LLP

(57) ABSTRACT

Apparatuses and methods relating to interfacing and controlling external batteries are described. In one embodiment, an external battery is integrated with a touch screen display. In one embodiment, the external battery provides an infrared communication link with a detachable device or system controller. In one embodiment, the external battery touch screen interface provides data received from a detachable device or system controller.

23 Claims, 38 Drawing Sheets

(51) Int. Cl.
*A61M 1/12* (2006.01)
*A61M 1/10* (2006.01)
*G06F 1/32* (2006.01)
*G08C 23/04* (2006.01)

(56) References Cited

U.S. PATENT DOCUMENTS

| | | | |
|---|---|---|---|
| 4,488,555 | A | 12/1984 | Imran |
| 5,215,523 | A | 6/1993 | Williams et al. |
| 5,300,027 | A | 4/1994 | Foote et al. |
| 5,383,840 | A | 1/1995 | Heilman et al. |
| 5,562,621 | A | 10/1996 | Claude et al. |
| 5,676,162 | A | 10/1997 | Larson, Jr. et al. |
| 5,704,891 | A | 1/1998 | Mussivand |
| 5,722,412 | A | 3/1998 | Pflugrath et al. |
| 5,767,659 | A | 6/1998 | Farley |
| 5,898,291 | A | 4/1999 | Hall |
| 5,993,993 | A | 11/1999 | Hall |
| 6,118,248 | A | 9/2000 | Gartstein et al. |
| 6,420,852 | B1 | 7/2002 | Sato |
| 6,427,088 | B1 | 7/2002 | Bowman, IV et al. |
| 6,597,948 | B1 | 7/2003 | Rockwell et al. |
| 6,733,455 | B2 | 5/2004 | Mo et al. |
| 6,744,152 | B2 | 6/2004 | Kroll |
| 6,835,491 | B2 | 12/2004 | Gartstein et al. |
| 6,892,096 | B2 | 5/2005 | Lyden |
| 6,958,706 | B2 | 10/2005 | Chaco et al. |
| 7,018,361 | B2 | 3/2006 | Gillespie et al. |
| 7,065,299 | B2 | 6/2006 | Schluter et al. |
| 7,089,291 | B1 | 8/2006 | Philyaw |
| 7,608,060 | B2 | 10/2009 | Gillespie, Jr. et al. |
| 7,625,662 | B2 | 12/2009 | Vaisnys et al. |
| 7,650,187 | B2 | 1/2010 | Gruber et al. |
| 7,668,731 | B2 | 2/2010 | Martucci et al. |
| 7,737,581 | B2 | 6/2010 | Spurlin et al. |
| 7,939,190 | B2 | 5/2011 | Colello et al. |
| 7,941,220 | B2 | 5/2011 | Tobacman |
| 8,131,365 | B2 | 3/2012 | Zhang et al. |
| 8,394,009 | B2 | 3/2013 | Bolyard et al. |
| 2004/0106954 | A1 | 6/2004 | Whitehurst et al. |
| 2006/0012334 | A1 | 1/2006 | Watson |
| 2007/0118186 | A1 | 5/2007 | Knauper |
| 2007/0202394 | A1 | 8/2007 | Viavattine |
| 2007/0255114 | A1 | 11/2007 | Ackermann et al. |
| 2008/0275590 | A1* | 11/2008 | Ross .............. 700/228 |
| 2008/0300659 | A1 | 12/2008 | Matos |
| 2009/0156885 | A1 | 6/2009 | Morello et al. |
| 2010/0145146 | A1 | 6/2010 | Melder |
| 2011/0063119 | A1 | 3/2011 | Martin et al. |
| 2011/0160516 | A1 | 6/2011 | Dague et al. |
| 2011/0218383 | A1 | 9/2011 | Broen et al. |
| 2011/0218384 | A1 | 9/2011 | Bachman et al. |
| 2011/0218385 | A1 | 9/2011 | Bolyard et al. |
| 2011/0320130 | A1 | 12/2011 | Valdes et al. |
| 2012/0001483 | A1 | 1/2012 | Bergefjord |
| 2012/0130153 | A1 | 5/2012 | Bolyard et al. |
| 2012/0188076 | A1* | 7/2012 | McSheffrey .......... 340/539.17 |
| 2012/0226350 | A1 | 9/2012 | Rudser et al. |
| 2012/0227002 | A1 | 9/2012 | Tiwari et al. |
| 2013/0127980 | A1 | 5/2013 | Haddick et al. |
| 2013/0204227 | A1* | 8/2013 | Bochenko et al. ........ 604/506 |
| 2013/0331899 | A1* | 12/2013 | Pearce et al. .................. 607/6 |
| 2014/0296614 | A1* | 10/2014 | Bolyard et al. ................ 600/16 |

\* cited by examiner

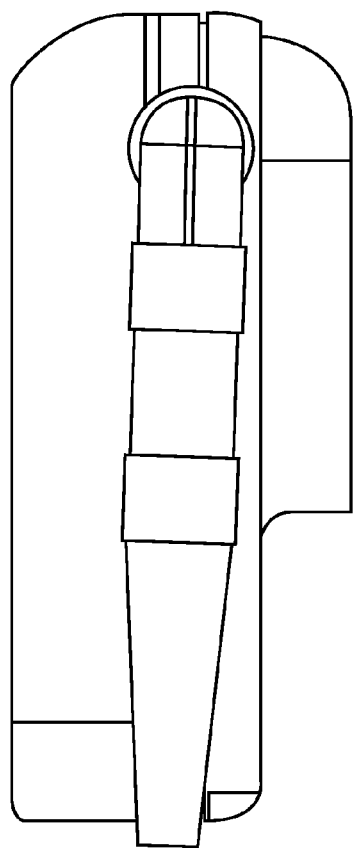
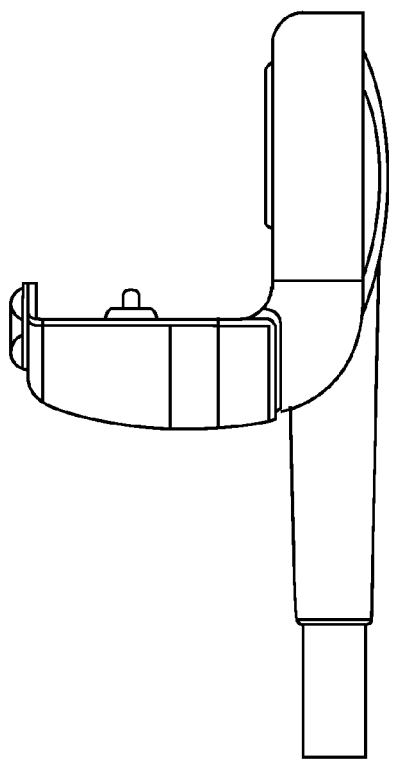
FIG. 18

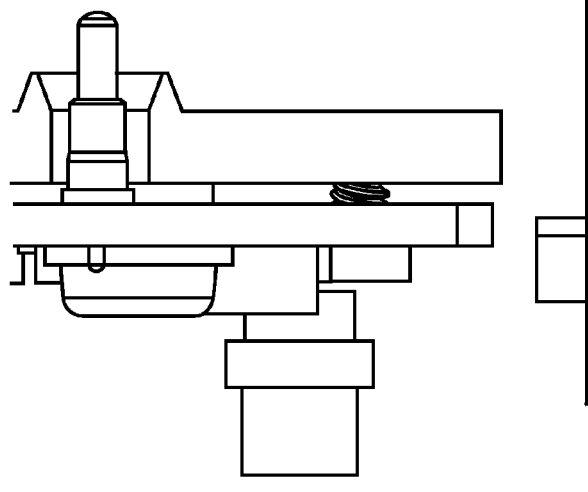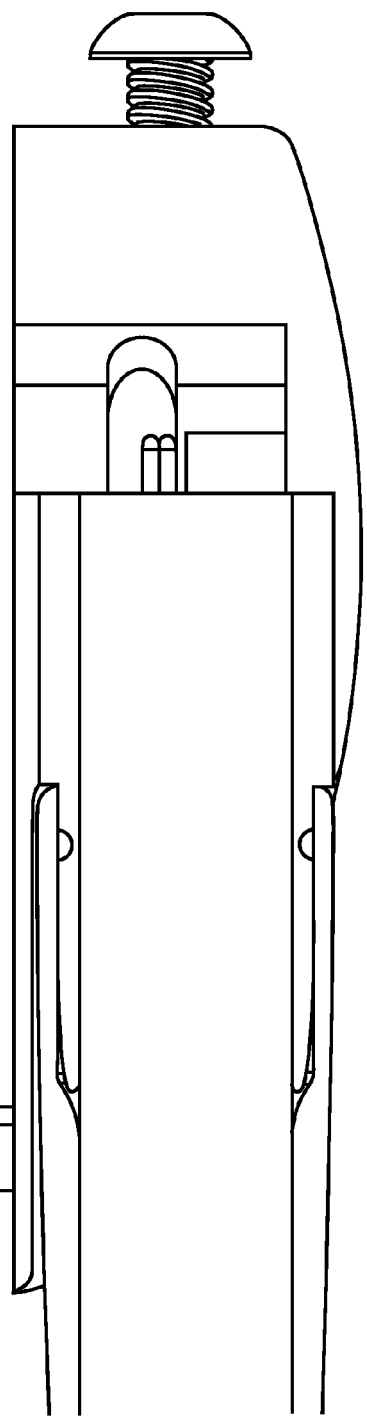
FIG. 29

TOUCH SCREEN INTERFACE AND INFRARED COMMUNICATION SYSTEM INTEGRATED INTO A BATTERY

CROSS-REFERENCE

This application is a continuation of U.S. patent application Ser. No. 13/894,284 filed on May 14, 2013, now issued as U.S. Pat. No. 8,827,890, which claims the benefit of U.S. Provisional Application Ser. No. 61/648,428, filed on May 17, 2012, and this provisional application is hereby incorporated herein by reference.

FIELD

Embodiments described herein generally relate to an external battery.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies: Copyright 2012, Thoratec Inc., All Rights Reserved.

BACKGROUND

Users of portable devices generally prefer small and light devices to larger, heavier alternatives. Portable medical devices such as controllers of mechanical circulatory systems (MCS) are carried on a person at all times and thus benefit greatly from a small portable design. One type of MCS is a ventricular assist device (VAD). A challenge for manufacturers is to reduce the size and weight of devices while still providing the reliability and ease of usability that users expect.

VADs are implanted in a patient and controlled by a system controller through a percutaneous connection. The VAD comprises a heart pump to provide assisted blood flow for a patient. A percutaneous (drive line) connection couples the system controller, comprising a motor controller and one or more batteries, to the implanted heart pump. Ventricular assist systems with their coupled system controller must provide for uninterrupted blood flow assistance for the patient (user) and therefore benefit from a design that is portable as well as robust.

VADs have typically been implanted for use in late stage heart failure (Class IV) patients. Some VAD systems allow patients to carry a portable system controller and batteries to allow for untethered operation of their heart pump. Typically, these patients can attain a high degree of mobility and freedom, as demonstrated by quality of life measures, however the peripheral devices (including the system controller and batteries) the patients must carry and manage remain cumbersome. Adoption of VAD systems is expected to expand to include less-sick (i.e. Class III) heart failure patients. Patient quality of life will be a significant factor in determining VAD acceptance with Class III patients. Therefore, more robust and intelligent device connections are needed to provide decreased risk of infection, decreased risk of power faults, and greater ease of use for patients.

Current VAD systems are easily identifiable as a medical device and can require two or more large batteries worn on the patient. Often each battery is coupled to the system controller by a long cable connection to allow for even weight distribution of each battery located externally from the system controller. More cables, connections, and weight create a greater likelihood of trauma to the exit site during routine movements of the patient. It is preferable for patients to have a device small enough to conceal beneath clothing. Also, from a quality of life perspective, patient worn peripherals should be as unobtrusive to the patient as possible. VAD cables can tangle and cause undue stress to an exit site where the percutaneous connection leaves the body. Stress at the exit site leads to skin breakdown or trauma and put the patient at risk of infection. Furthermore, the current cables and electrical connections result in components that are susceptible to water, dust or other elements. Devices having multiple exposed electrical connections also contain a higher risk of shorting out the medical device through unintended connections. Patients using current systems must take special care when maintaining and using their devices.

Current medical devices also do not allow for multiple input and output options for their medical devices. Patients must choose systems with advanced touch screen interfaces that are relatively large, or choose smaller but potentially less flexible displays with separate buttons or switches. Therefore, greater flexibility for VAD systems is needed in order to allow their device to be as portable as possible in certain situations, without sacrificing usability.

SUMMARY OF THE DESCRIPTION

In one embodiment, a data connection is established between an external battery and a detachable device (e.g., a patient device or system controller). In one embodiment, the external battery provides power to the detachable device and a data communication link is established between the external battery and detachable device. In one embodiment, a representation of data sent between the external battery and the detachable device is displayed on a touch screen integrated into the external battery. In one embodiment, the external battery can provide power to the detachable device, which can be a system controller for an MCS such as a left ventricular assist device, and can also provide power to the MCS; in one embodiment, the power is provided only after a wireless (e.g., infrared) data connection is established between the detachable device and the external battery.

In one embodiment, a removable external battery with an integrated touch screen display is coupled to a system controller. In one embodiment, the display on the external battery provides additional or duplicate status as the system controller.

In one embodiment, a system controller and an external battery are communicatively coupled together with an infrared data link.

In one embodiment, the system controller can send and receive data from the external battery through the infrared data link. In one embodiment, the data is one or more of alarm status, event history, pump parameters, log data, and power source status. In one embodiment, pump parameters are one or more of estimated fluid (e.g., blood) flow in the pump, fluid (e.g., blood) pressure, voltage values, phase current, and quiescent (IQ) current.

In one embodiment, the system controller controls a heart pump, and data associated with the heart pump is sent and received by the external battery. In one embodiment, the external battery displays data on an integrated touch screen that is integrated with a display on the external battery.

In one embodiment, the external battery provides power to the system controller after establishing the infrared data link. In one embodiment, power provided by the external battery is a secondary power source for the system controller.

In one embodiment, magnets, electromagnets or mechanical connections between the components in a system allow for a controlled breakaway sequence. In one embodiment, a power adapter, system controller, and external battery implement a controlled breakaway connection system such that the power adapter is the first component to breakaway when the system is under external mechanical stress.

BRIEF DESCRIPTION OF THE DRAWINGS

The present invention is illustrated by way of example, and not by way of limitation, in the figures of the accompanying drawings in which like references indicate similar elements.

FIG. 18 is a projected view illustrating one embodiment of a system controller coupled to a percutaneous lead and decoupled from a power adapter;

FIG. 29 is a projected view illustrating one embodiment of a power adapter power cable, power connection and magnets;

DETAILED DESCRIPTION

Various embodiments and aspects of the invention(s) will be described with reference to details discussed below, and the accompanying drawings will illustrate the various embodiments. The following description and drawings are illustrative of the invention and are not to be construed as limiting the invention. The term "coupled" as used herein, may mean directly coupled or indirectly coupled through one or more intervening components. Numerous specific details are described to provide a thorough understanding of various embodiments of the present invention. However, in certain instances, well-known or conventional details are not described in order to provide a concise discussion of embodiments of the present inventions.

Overview

Figure 1:
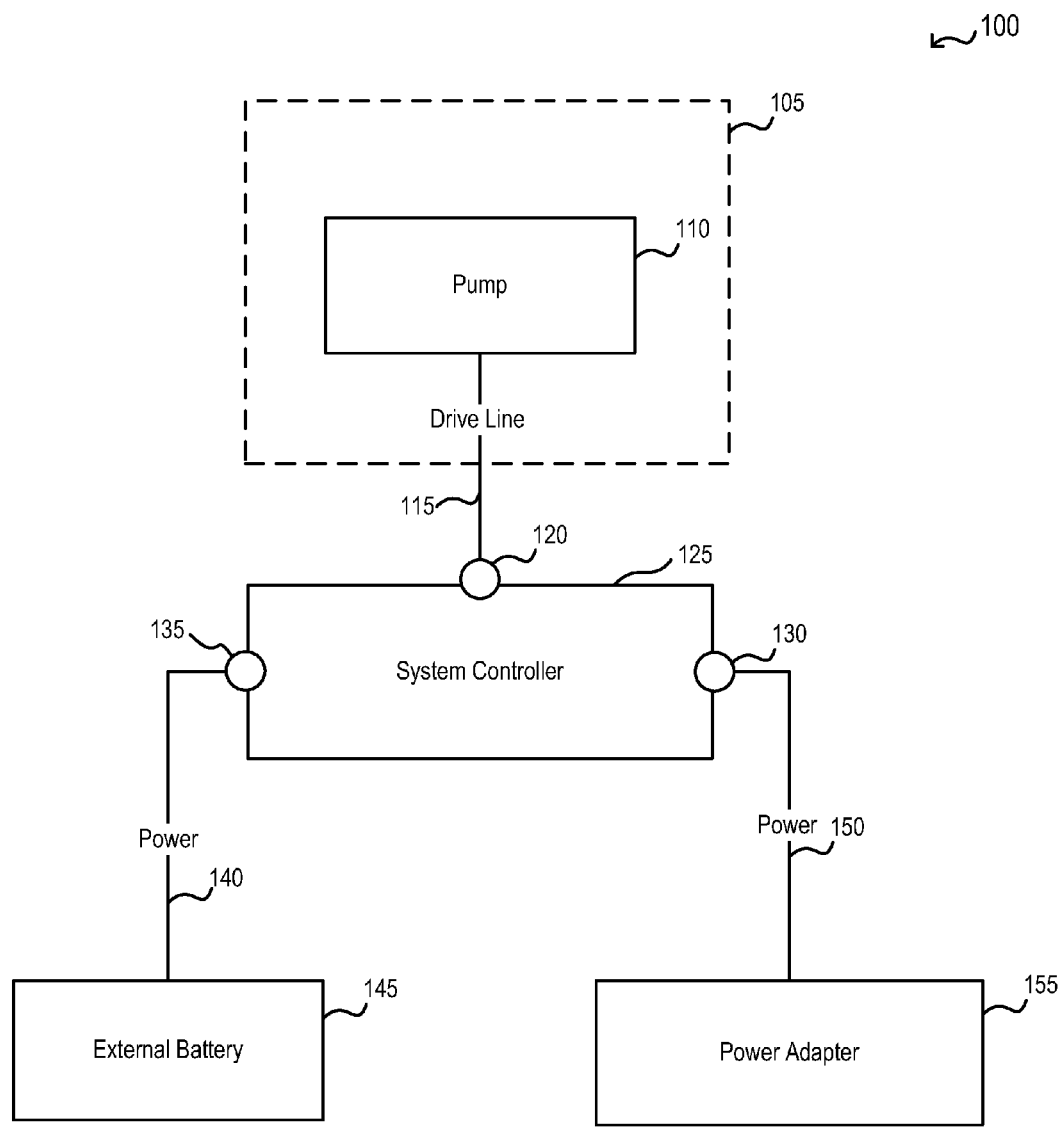
FIG. 1 illustrates, in block diagram form, an exemplary ventricular assist system connecting a pump, system controller, external battery, and a power adapter (such as an adapter that can charge the external battery and a battery within the system controller)

Throughout the description, the methods, apparatuses, and systems of the present invention are discussed in the context of a ventricular assist system (VAS, such as a left ventricular assist device (LVAD)). It will be appreciated, however, that these methods, apparatuses, and systems are equally applicable to other types of mechanical circulatory systems (MCS). FIG. 1 illustrates one embodiment of a ventricular assist system (VAS) including a pump 110, system controller 125, external battery 145, and power adapter 155. In one embodiment, pump 110 is a heart blood pump (e.g., a rotary or similar pump for providing flow of blood) implanted in the user. In one embodiment, pump 110 assists a patient's heart to maintain a steady flow of blood throughout their body. Pump 110 continuously offloads blood from the left ventricle of the heart and propels the blood into the aorta at a steady rate controlled by system controller 125.

In one embodiment, system controller 125 provides interface and control functions for pump 110. One of skill in the art, however, will recognize system controller 125 can control any device operative by an external controller. In one embodiment, system controller 125 provides one or more of the functions of motor commutation, power management, condition sensing, data logging and communication, and/or user input/output. In an exemplary embodiment, system controller 125 is coupled to drive line 115 (percutaneous lead) coupling pump 110 to system controller 125.

In one embodiment, system controller 125 can connect to external battery 145 and power adapter 155 by connections 135 and 130, respectively. In one embodiment, connections 135 and 130 are one or more of electromagnetic, magnetic, or mechanical ports that allow for a controlled breakaway sequence when stress is applied to any of the system components. Further details of connections 135 and 130 and various embodiments of a controlled breakaway sequence are described below.

In one embodiment, the system controller's drive line 115 connection design allows for 360-degree axial rotation intended to minimize trauma to the exit site, and reduce torsional stress on the drive line. Stress on the exit site can cause skin trauma leading to greater risk of infections. Reduced stress on drive line 115 improves cable management for a patient and allows for greater freedom of movement.

System Controller

Figure 2:
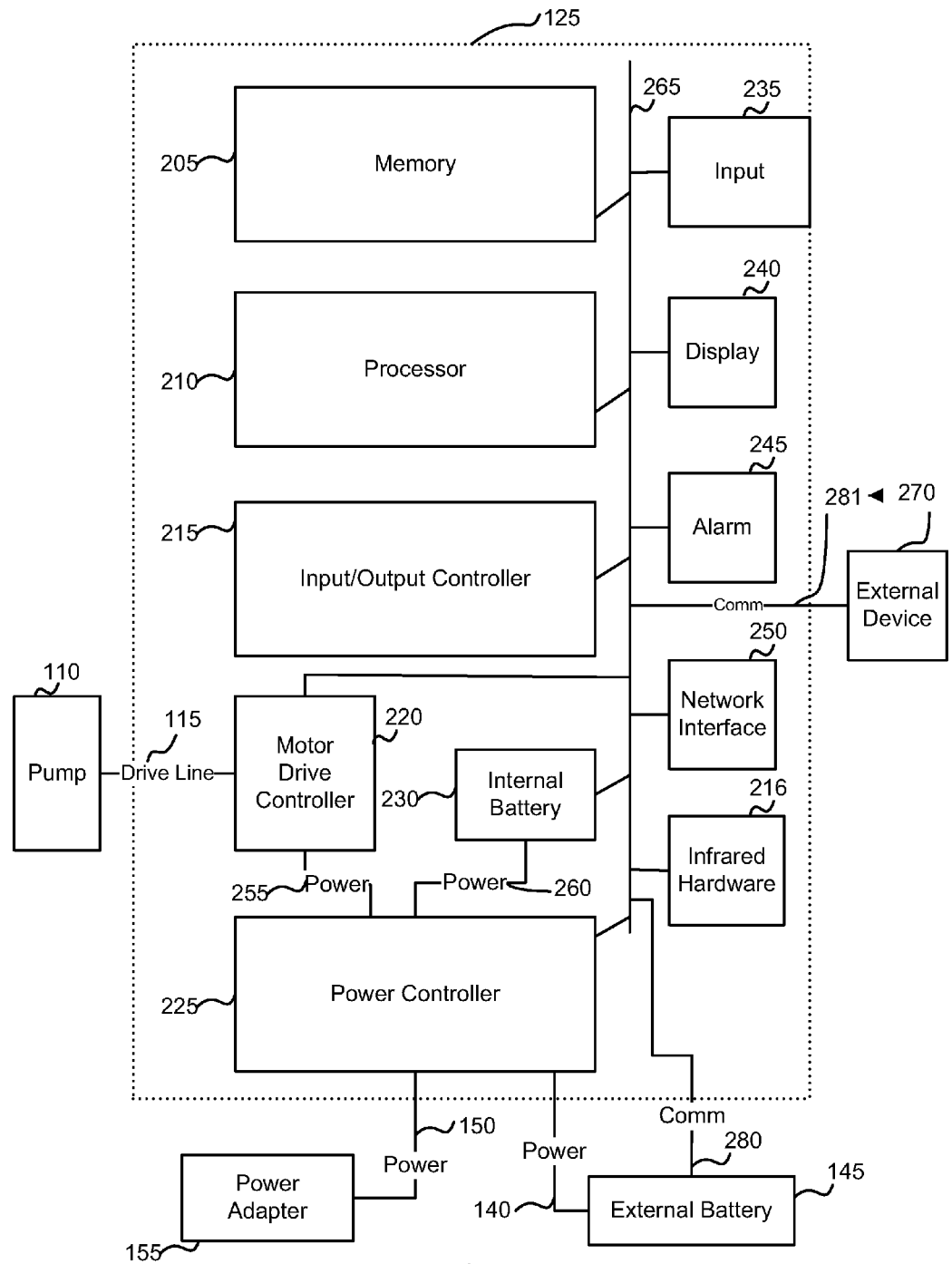
FIG. 2 illustrates, in block diagram form, an exemplary system controller.

FIG. 2 illustrates an exemplary system controller 125 that can detect, store, and utilize system-operating parameters associated operation of pump 110. In one embodiment, system controller 125 maintains constant communication and control over an external motor in external pump 110. System controller 125 can provide power to and regulate the speed of pump 110 through electrical signals transmitted by a percutaneous lead (drive line 115) extending through the skin of patient 105 with pump 110 implant. System controller 125 can also receive data back from pump 110 (e.g., electromotive force data or signals used to determine the speed of the pump). In one embodiment, system controller 125 provides one or more of interpreting and responding to system performance, performing diagnostic monitoring, indicating hazard and advisory alarms, providing a complete backup system, and event recording capability.

In one embodiment, one or more processors 210 in system controller 125 execute instructions in memory 205 to maintain the power and functions of pump 110. Processor 210 can be a programmable microcontroller, microprocessor or other similar device capable of executing instructions. Processor as used herein can refer to a device having two or more processing units or elements, e.g., a CPU with multiple processing cores. Memory 205 can include dynamic random access memory and a memory controller that controls the operation of the memory. Memory 205 can also include a non-volatile read only and/or re-writable memory for storing data and software programs. Memory 205 can contain a program or instructions that controls the operation of processor 210 and also can contain data used during the processing of controls for pump 110. In one embodiment further described below, memory 210 includes a computer program or instructions, which causes processor 210 to communicate to external battery 145.

In one embodiment, system controller 125 comprises one or more integrated batteries 230, power controller 225 and motor drive controller 220. Power controller 225 can regulate, control and/or manage power usage of system controller 125, motor drive controller 220 or other system controller 125 components. Power controller 225 can be connected to motor drive controller 220 by power connection 255. In one embodiment, external battery 145 and/or power adapter 155 is connected to system controller 125 to provide power in addition to or instead of internal battery 230. Power controller 225 can receive and distribute power from one or more of internal battery 230 (over power line 260), external battery 145 (over power line 140), or power adapter 155 (over power line 150). Power adapter 155 can be an AC/DC power adapter (e.g., a standard home plug adapter or other AC source adapter) or a DC power adapter (e.g., a car cigarette lighter adapter, or other DC source adapter). In one embodiment, motor 220 is coupled to drive line 115 to assist pump 110. In one embodiment, system controller 125 is a different type of detachable device, for example another type of medical device, consumer electronic device or other device that is detachable (e.g., able to be decoupled) from an external connection and/or external battery.

Memory 205, one or more processors 210, power controller 225 and input/output controller 215 can be separate components or can be integrated in one or more integrated circuits. The various components in system controller 125 can be coupled by one or more communication buses or signal lines 265.

In one embodiment, Input/Output controller 215 enables system controller 125 to communicate with external battery 145. In other embodiments further described below, memory 205 includes instructions for wireless communication with other data processing systems or devices (separate from or in addition to external battery pack 145). In one embodiment, memory 205 also includes instructions to implement the various other features of the system controller 125 described below.

System controller 125 can also include network interface 250. Network interface 250 allows system controller 125 to communicate, in one embodiment, to other processing systems through a wireless (e.g., Bluetooth, Infrared Data Association (IrDA), WiFi, or other) protocol. In one embodiment, network interface 250 implements a wireless interface such that no external physical connection is required for networking or external communication. Reducing or eliminating external wired connections is beneficial for maintaining a sealed waterproof or water resistant environment to house system controller 125. Network interface 250 is coupled to bus 265 so that system controller 125 can receive data, such as communication from an external device (e.g., tablet, personal computer, or external battery) and send data to/from processor 210 and memory 205.

In one embodiment, system controller 125 interfaces with an external battery comprising touch screen interface 330. In one embodiment, system controller 125 uses touch screen 330 to display system controller 125 notifications and status. Touch screen 330 can be a capacitive or resistive transparent input device that is overlaid on a display such as an LCD (Liquid Crystal Display) device such that the touch screen provides both input and output capabilities. System controller 125 can also have one or more integrated status displays separate from the display utilized through external battery 145. For example, system controller 125 can have various integrated displays (e.g., several LEDs) including one or more of a battery gauge, alarm notification, battery symbols, pump status, or other representations of VAS status.

In one embodiment, system controller 125 includes one or more input/output (I/O) devices and/or sensor devices. In one embodiment, I/O devices include one or more of display 240, an audio device (e.g., speaker), a vibration motor, input device (e.g., buttons, knobs, levers, dials or similar devices), and one or more alarms 245. I/O controller 215 interfaces with I/O devices integrated with or coupled with system controller 125. I/O devices can be coupled to bus 265 and can send and receive data from I/O controller 215. I/O controller 215 can also interface with external devices through input 235.

In one embodiment, display 240 is a segment display, LED display, full-area 2-dimensional display or other display capable of providing a user with visual indication of status or performance of system controller 125.

In one embodiment, system controller 125 includes circuitry and sensors for supporting a positioning system, such as that provided by the global positioning system (GPS), a cellular communication system, accelerometer, compass, wireless network, or other method for determining the geographic positioning or relative movement. In one embodiment, system controller 125 records positioning information of system controller 125 (e.g., from an accelerometer or GPS). In one embodiment, system controller 125 utilizes positioning information to estimate and record patient activity levels. In one embodiment, patient activity information is stored in memory 205 and can be retrieved or sent to an external device. Recording patient activity levels for later analysis by a medical professional can improve quality of patient care by providing a record of patient activity. Otherwise, a medical professional or technician must instead rely upon the patient's memory to recall past events and estimated activity levels.

In one embodiment, system controller 125 generates diagnostic information. Diagnostic information is stored in memory 205 for real time analysis or later retrieval and analysis by an external device (data processing system, tablet, computer, specialized device).

System controller 125 receives user or patient input and output information through a user interface. In one embodiment, system controller 125 has a segmented display and/or one or more LED or other type of light to indicate status. In one embodiment, symbols or icons on system controller 125 are backlit when their status is active. For example, a power symbol icon may be used to indicate power status. A red heart symbol can be used to show overall status of the heart pump. An audio symbol button can be used to silence alarms. A series of lights can be used to indicate battery level or charge status. A battery icon can be used to show health of the battery.

In one embodiment, system controller 125 is mechanically coupled to external battery 145. In one embodiment, external battery 145 is able to send and receive data to system controller 125 via one or more wireless communications link (e.g., infrared). A wireless transfer protocol (e.g., infrared) obviates the need for a wired link between system controller 125 and external battery 145 to facilitate a waterproof enclosure while retaining a robust mechanical design (i.e., no electromechanical connector). In one embodiment, system controller 125 uses infrared hardware 216 to communicate through infrared with external battery 145 which includes infrared hardware 316. In one embodiment, infrared hardware 216 and 316 are infrared transceivers that allow for infrared data communication between two or more devices.

In one embodiment, system controller 125 includes network interface 250 for one or more wireless protocols (e.g., Bluetooth, Infrared, WiFi, or other form of wireless communication link). Network interface 250 allows system controller 125 to communicate to other data processing systems or devices through a wireless network connection. In one embodiment, wireless network interface 250 is used so that the need for external physical connections can be minimized or entirely removed. Reducing or eliminating external wired connections is beneficial for maintaining a sealed waterproof or water resistant environment to house system controller 125. In one embodiment, network interface 250 is coupled to bus 265. In one embodiment, bus 265 is coupled to processor 210 and memory 205 of system controller 125. In one embodiment, network interface 250 sends and receives data to one or more of external battery 145 and/or external device 270 (e.g., tablet, personal computer, PDA, smartphone, specialized medical device, or other data processing system).

In one embodiment, external device 270 connects to system controller 125 to download and/or upload data stored in memory 205 of system controller 125. In one embodiment, external device 270 sets, changes, and/or receives pump 110 parameters. In one embodiment, pump 110 parameters include one or more of pump speed, estimated flow, DC bus voltage, phase current, and quiescent current. For example, in a clinical setting a technician can wirelessly connect from external device 270 to system controller 125 to setup the VAS for the first time, and/or to make changes to existing pump 110 settings. By using external device 270, a technician can manage pump 110 settings of system controller 125 to start, stop or otherwise modify the operation of pump 110. In other embodiments, external device 270 can upload or update commands, firmware, software and/or programs on system controller 125.

In one embodiment, external device 270 sets, changes, and/or receives other parameters (separate from pump control). In one embodiment, other parameters include one or more of accelerometer data, alarm information, log data (including alarm and event history), power source status, power source runtime information, and other data. In one embodiment, once a parameter is set or changed, the updated parameter(s) are stored in memory 205 such that decoupling system controller 125 from the external device 270 maintains parameter(s) in system controller 125.

Wireless transfer of data between system controller 125 and external devices facilitates efficient patient management. In one embodiment, external device 270 described above is a base station used by a clinician or medical professional to monitor the VAS and patient. The base station can receive and send the data and parameters to system controller 125 as described above. In one embodiment, the base station is configured to mirror the alarms and notifications of system controller 125. In one embodiment, base station uploads commands to modify settings of system controller 125 and receives real time feedback as to the success of the commands.

In one embodiment, data and parameters on system controller 125 are sent to external battery 145. In one embodiment, external battery 145 receives data from system controller 125 and outputs the data to a display on external battery 145. Further details regarding the data displayed on the external battery 145 are discussed below.

External Battery

Figure 3:
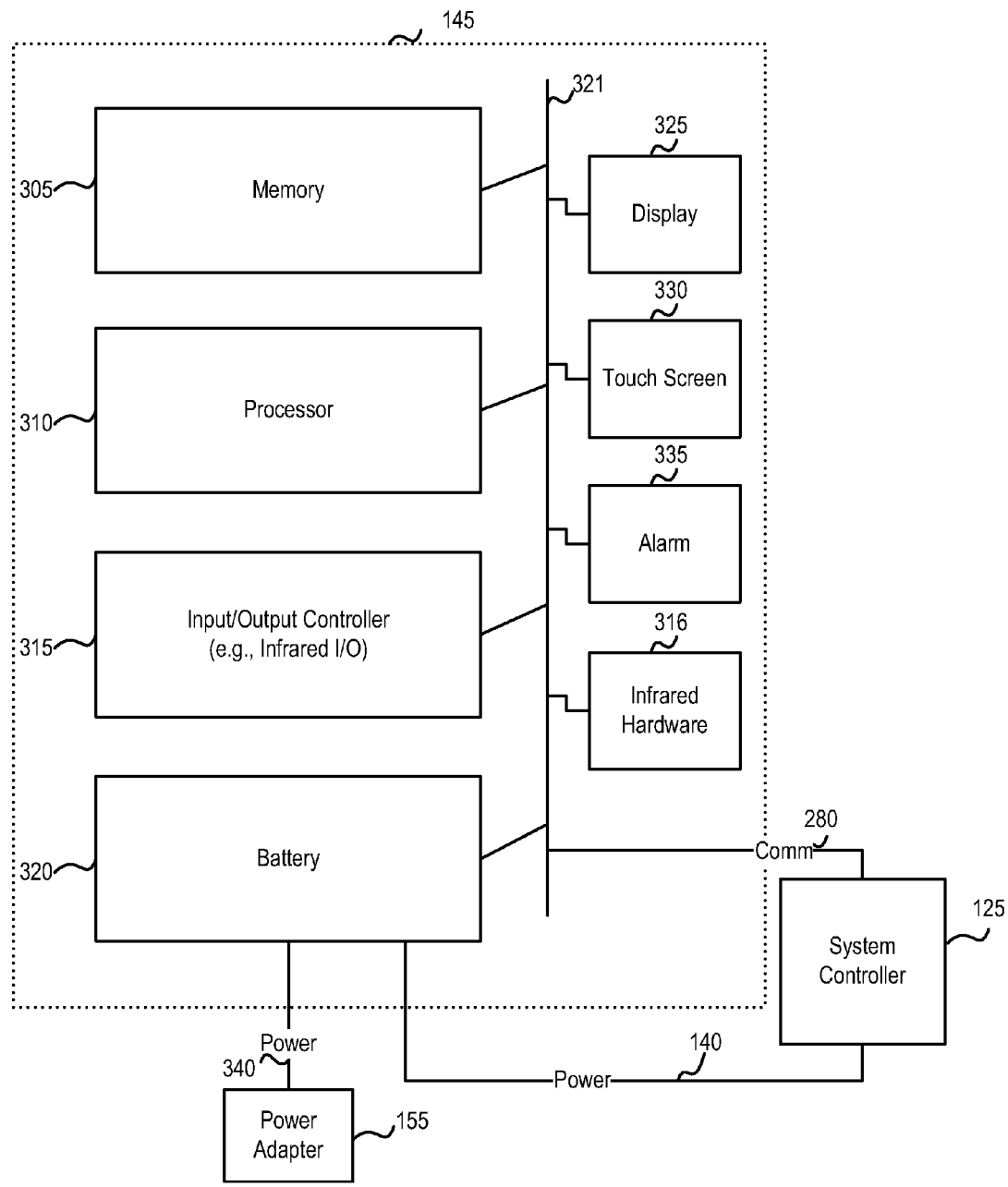
FIG. 3 illustrates, in block diagram form, an exemplary external battery for use with a system controller.

FIG. 3 illustrates an exemplary external battery 145 with touch screen 330 for use with system controller 125. In one embodiment, one or more processors 310 in external battery 145 executes instructions in memory 305 to establish and maintain communication with system controller 125, receive input from touch screen 330 and output data to display 325. Processor 310 can be a programmable microcontroller, microprocessor or other similar device capable of executing instructions. Processor as used herein can refer to a device having two or more processing units or elements, e.g., a CPU with multiple processing cores. In one embodiment, external battery 145 includes memory 305. Memory 305 can include dynamic random access memory (DRAM) and a memory controller that controls the operation of the memory. Memory 305 can also include a non-volatile read only and/or re-writable memory for storing data and software programs. Memory 305 can contain a program or instruction set that controls the operation of processor 310. For example, memory 305 can be a non-transitory computer readable storage medium that stores one or more computer programs that when executed by processor 310 perform one or more methods described herein such as the methods shown in FIG. 4 or 7 or 8. Memory 305 can also contain data or instructions used during communication with system controller 125 and data or instructions for operating touch screen 330 and display 325. Touch screen 330 is capable of receiving direct user input through touch (e.g., touch of a human user's finger(s)) and/or, a stylus. Display 325 is capable of providing visible output to the user. In one embodiment, touch screen 330 and display 325 are integrated into one unit, an example of which is shown as touch screen 610 in FIG. 6. In one embodiment further described below, memory 305 includes a computer program or instructions, which causes processor 310 to control alarm 335. In one embodiment, alarm 335 includes one or more hazard alarms mirrored from system controller 125.

External battery 145 includes one or more integrated batteries 320. In one embodiment, external battery 145 provides supplemental power to system controller 125. In the case of failure or removal of external battery 145, system controller 125 can automatically switch to internal battery 230 and continue to provide power and control for pump 110. In one embodiment, power adapter 155 can be coupled to external battery 145 to charge one or more integrated batteries 320. Memory 305, one or more processors 310, touch screen 330, display 325, and one or more alarms 335 can be separate components or can be integrated in one or more integrated circuits. Alarm 335 can include one or more of a speaker for output of audio, motor for providing vibration, and visual on display 325. One or more communication buses or signal lines 321 can couple the various components in external battery 145.

In one embodiment, Input/Output controller 315 enables external battery 145 to communicate with system controller 125. In other embodiments further described below, memory 305 includes instructions for wireless communication with other data processing systems or devices (separate from the system controller 125). In one embodiment, memory 305 also includes instructions to implement the various other features of the external battery pack 145 described below.

In one embodiment, external battery pack 145 contains integrated touch screen 330 and display 325. Touch screen 330 on external battery 145 enables a user to request and receive updates from system controller 125 and external battery 145 without the need for accessing controls on system controller 125. In one embodiment, pump 110 parameters from system controller 125 are received and displayed on touch screen 330. In one embodiment, touch screen 330 can display a representation of one or more of pump speed, estimated flow, power measurement, and a pulsatility index parameter.

In one embodiment, touch screen 330 configures or displays alarm information on system controller 125. Further details on the alarm on system controller 125 as well as the ability to mirror alarms on external battery 145 are discussed below. System controller 125 can log time-stamped data and events (e.g., power source changes, suction events, and other events) that can be output to touch screen 330. In one embodiment, touch screen 330 can present a series of the most recent events to assist in remote or local troubleshooting. For example, a patient on the phone with a technician can recall the last set of events that occurred on system controller 125 in order to discuss VAS history with a remote technician. In one embodiment, touch screen 330 has a user interface that includes multiple screens and menu options for accessing information related to system controller 125 and/or one or more other device(s) connected to external battery 145. For example, alarm history, trending data, power source runtime information and other details can be accessible through touch screen 330 interface.

Touch screen 330 on external battery 145 allows for system controller 125 to be designed with less weight, size, and electrical complexity. As discussed above, system controller 125 provides critical monitoring and control of heart pump 110. Locating potential points of failure to a less critical and easily replaceable external battery 145 extends the longevity and reliability of system controller 125. For example, external battery 145 can be decoupled to allow for the smallest form factor possible during stand-alone operation system controller 125. In one embodiment, while external battery 145 is decoupled, system controller 125 automatically switches to internal battery 230 and pump 110 continues to operate.

In addition, relegating a heavily used component (touch screen 330 interface) to a relatively inexpensive and easily replaceable external battery 145 provides less wear and tear on system controller 125. Furthermore, the fact that touch screen 330 is located externally from system controller 125 minimizes the possibility that damaging touch screen 330 will electrically affect the system controller's functionality. An external touch screen 330 also minimizes interactions between the software driving system controller 125 and the software driving touch screen 330.

As discussed above, one embodiment of system controller 125 has a user-interface consisting of buttons (e.g., pushbuttons) and a display (e.g., LED). Replacing buttons and a display with touch screen 330 large enough for large icons and written textual descriptions and icons would be prohibitively large for system controller 125. Integrating touch screen 330 with large battery maintains the portability of system controller 125 when external battery 145 is decoupled.

In one embodiment, integrating touch screen 330 and glass/plastic front screen cover into external battery 145 reduces the weight of system controller 125 by more than half. Separating touch screen 330 from system controller 125 also provides benefits in terms of programming extensibility, regulatory compliance, and failure mode analyses. Using a separate processor 310 from processor 210 in system controller 125 allows the icons, screen layouts, text language, and other options to be changed without altering the instructions or programs of system controller 125. Other display 325 related modifications include one or more of adding additional language support, user interface modifications to accommodate the latest clinical usages and needs, and allowing users to view the heart pump's operational data/history. Touch screens are typically subject to heavy use and can be subjected to excessive pressure by users. Touch screens may also be susceptible to scratching and cracking of the glass or plastic housing. Separating touch screen 330 from system controller 125 allows system controller 125 to continue operating unaffected if touch screen 330 or display 335 are damaged. In one embodiment when processor 310 in external battery 145 is damaged or suffers from instruction errors/faults, system controller 125 and external battery 145 are unaffected. Because system controller 125 and external battery 145 are separated by an infrared communications link, there is no possibility of touch screen 330 or display 325 electrically interfering with the system controller's operation of pump 110. A damaged external battery 145 is easily replaced with a new external battery 145 without interruption of pump 110. In one embodiment, external battery 145 or other similarly connected device cannot change controls related to pump 110 but can receive status updates or pump 110 statistics.

Figure 4:
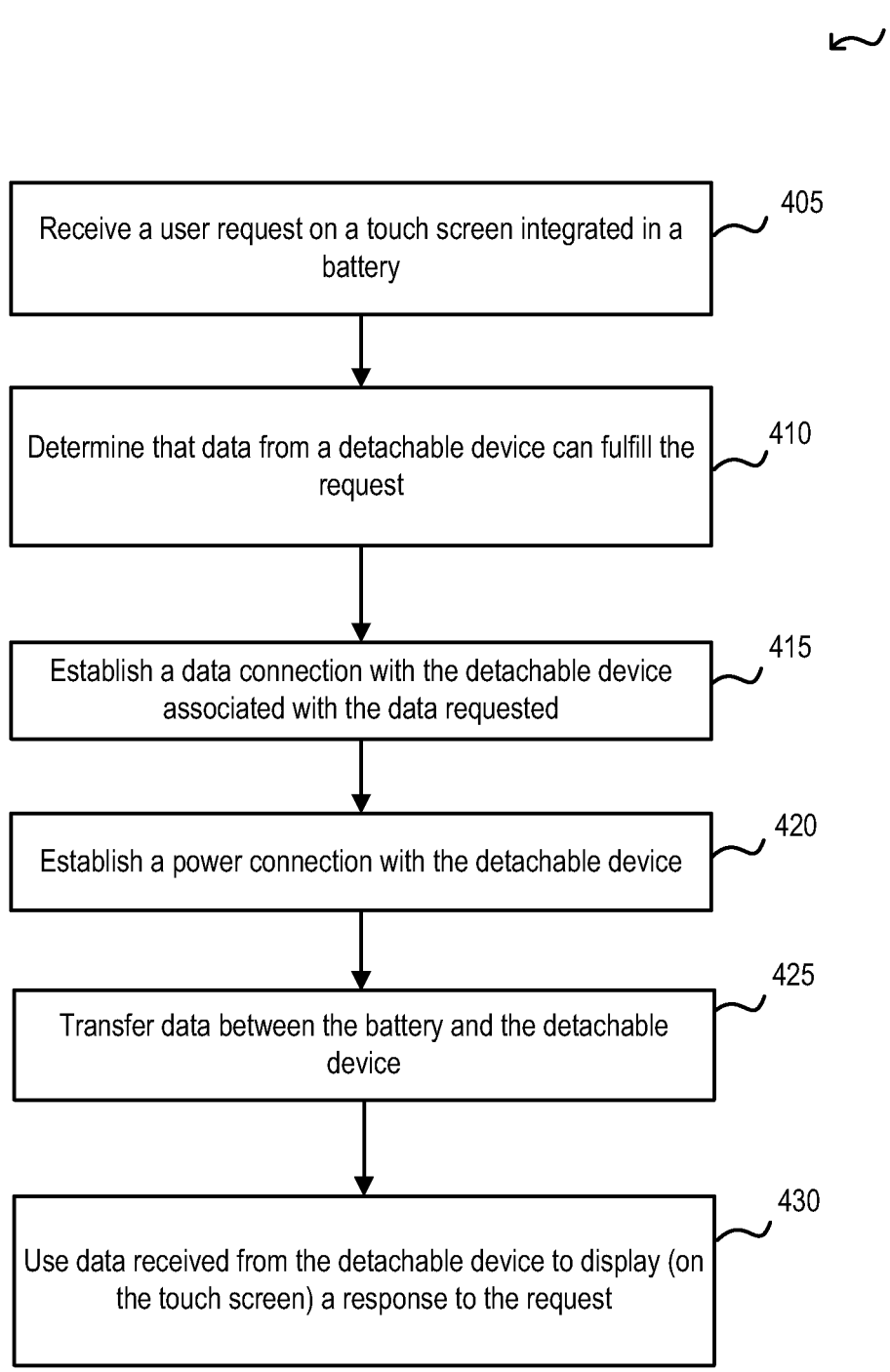
FIG. 4 is a flow chart illustrating a method for interacting with the touch screen integrated into an external battery pack.

FIG. 4 is a flow chart illustrating an exemplary method 400 for receiving and displaying data on a touch screen integrated into a battery. For example, method 400 may be performed by external battery 145.

At block 405, external battery 145 receives a request on integrated touch screen 330. In one embodiment, the user or patient touches touch screen 330 on external battery 145 to make a selection. In other embodiments, the patient uses a stylus or other interface to make a selection on the screen. For example, the patient may request the status of pump 110 (e.g., current blood flow estimation) by pressing on a pump icon represented on touch screen 330.

At block 410, external battery 145 determines that data from a detachable device can fulfill the request initiated on touch screen 330. In one embodiment, the detachable device is system controller 125. For example, current blood flow estimation can be determined by data received or read from system controller 125.

At block 415, external battery 145 establishes a data connection between external battery 145 and a detachable device (e.g., system controller 125). This data connection can be through infrared hardware on both system controller 125 and external battery 145. In one embodiment, external battery 145 requests data from system controller 125 after receiving input on touch screen 330. In other embodiments, system controller 125 detects the connection to external battery 145 and provides a stream of relevant and associated data to external battery 145 such that system controller 125 does not need to process requests. For example, upon detecting that external battery 145 is connected, system controller 125 provides real time updates to external battery 145 and external battery 145 can store the updates in memory 305 for processing by processor 310.

At block 420, external battery 145 establishes a power connection between external battery pack 145 and the detachable device. In one embodiment, a power connection is created after determining that a data connection to the detachable device is established.

At block 425, external battery 145 transfers data between external battery 145 and the detachable device. In one embodiment, external battery 145 requests data from the detachable device. In other embodiments, the detachable device provides a stream of real time data and external battery 145 processes all data and displays only requested or relevant data to the user.

At block 430, external battery 145 processes data received from the detachable device. In one embodiment, external battery 145 formats the processed data for display on display 325. For example, after a request for blood pump flow information, the current blood pump flow is displayed on touch screen 330.

Redundant and Safe Power Management

In one embodiment, system controller 125 provides uninterrupted power to motor 220 during power source exchanges (e.g., switching from external battery 145 to power adapter 155, removing both external battery 145 and power adapter 155, or other combinations thereof). In one embodiment, the primary power source for system controller 125 is one of external battery 145 and power supply 155. In one embodiment, a secondary power source (e.g., battery 230, which can be a lithium-ion battery) is integrated within the main body of system controller 125 housing. Removal of either of the primary power sources automatically causes system controller 125 to switch to internal battery 230 for power such that there is no interruption of motor drive controller 220 and pump 110.

In one embodiment, internal battery 230 provides uninterrupted operation for system controller 125 and pump 110 when all external power sources (e.g., external battery 145 or power adapter 155) are decoupled from system controller 125. Internal battery 230 allows system controller 125 and pump 110 to withstand the failure, or removal of all external power sources. For example, in certain situations a user or patient may prefer to remove all external devices and external battery packs to achieve maximum portability of system controller 125.

Figure 5:
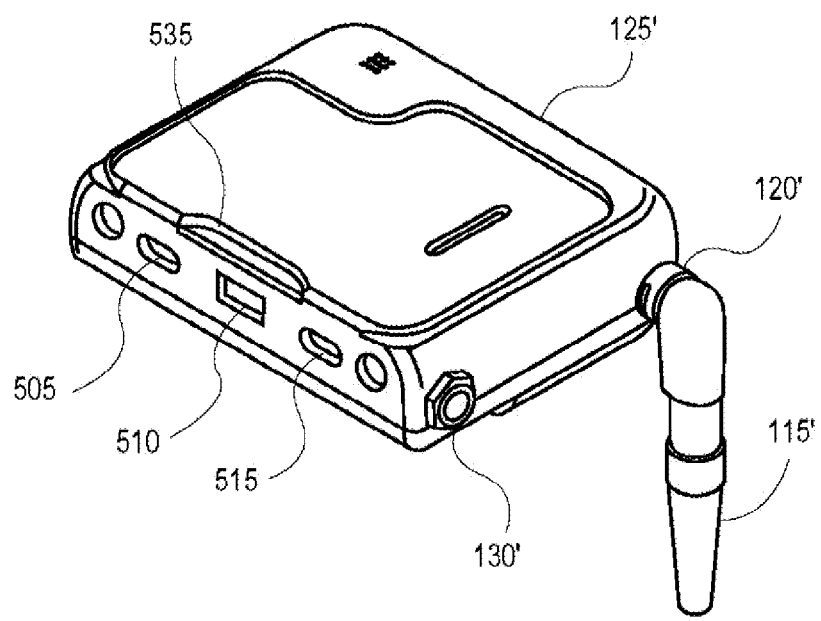
FIG. 5 is a projected view illustrating one embodiment of a system controller.

FIG. 5 illustrates, as a three-dimensional drawing, an exemplary system controller 125'. In one embodiment, system controller 125' includes integrated infrared port 510 protected by a translucent window. The infrared port 510 can be implemented as part of infrared hardware 216 shown in FIG. 2. In one embodiment, system controller 125' connects to external battery 145 that also contains an infrared port behind a window. In one embodiment, infrared port on external battery 145 can be implemented as part of infrared hardware 316 shown in FIG. 3. System controller 125' has one or more power connections to couple system controller 125' to an external source of power. System controller 125' can have separate power connections to connect to an external battery as well as to connect to a power adapter. In one embodiment, system controller 125' has one or more power connections 505 and 515 to enable connection to external battery 145.

Figure 6:
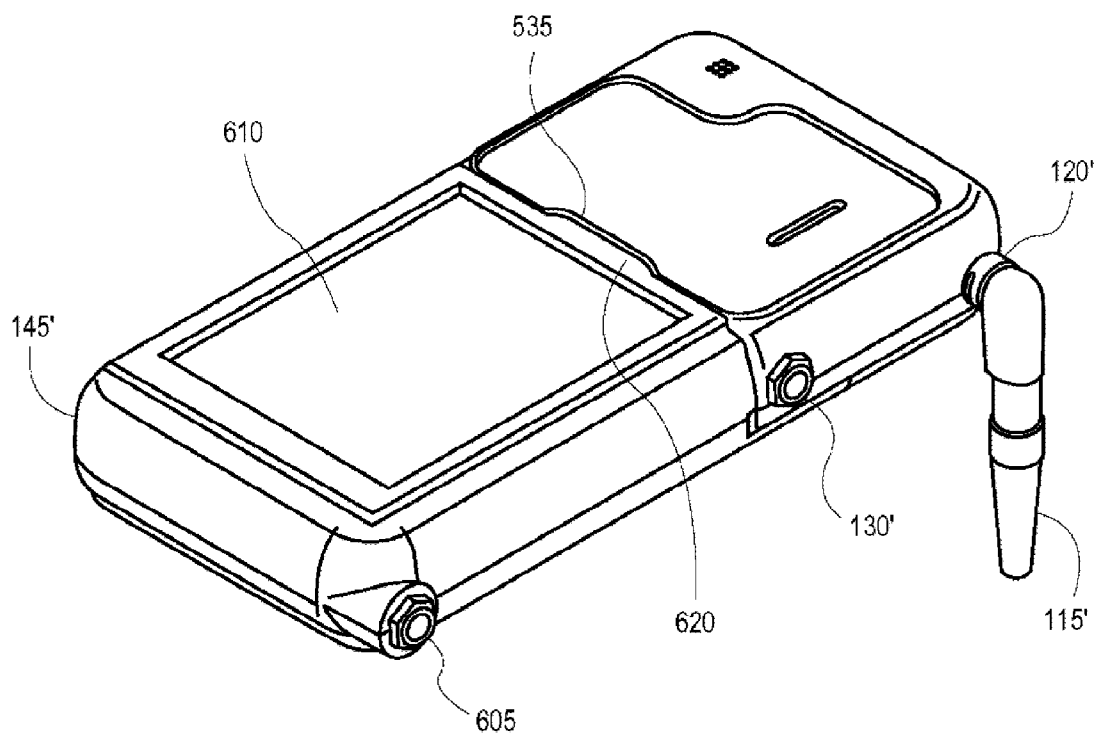
FIG. 6 is a projected view illustrating one embodiment of a system controller further coupled to an external battery.

FIG. 6 illustrates, as a three-dimensional drawing, an exemplary system controller 125' coupled to an exemplary external battery 145'. In one embodiment, system controller 125' has power connection 130' separate from external battery 145' connection 605. In one embodiment, system controller 125' contains recessed area 535 above infrared port 510 to receive an overhang or lip 620 from external battery 145' to further shield infrared port 510 from outside interference when system controller 125' and external battery 145' are communicatively coupled.

In one embodiment, external battery 145' includes integrated touch screen 610, and breakaway connection 605 to enable external battery 145' to couple to power adapter 155 or other power source. In one embodiment, breakaway connection 605 integrated into external battery 145' is a separate connection from system controller breakaway connection port 130'. In one embodiment, power adapter breakaway connection 605 on external battery 145' and breakaway connection 130' on system controller 125' are able to receive the same or compatible connector/plug from power adapter 155 or other external power source. System controller 125' also contains port 120' that couples drive line 115' to system controller 125'. In one embodiment, drive line port 120' is a separate component and is physically incompatible with breakaway connection ports 130' and 605.

In one embodiment, power connections 505 and 515 coupling system controller 125' and external battery 145' together are one or more of an electromagnet, magnet, and mechanical connection (herein after simply referred to as a breakaway power connection). In one embodiment, breakaway power connections 130' and 605 from power adapter 155 connect directly to system controller 125' housing and no power leads are required. In one embodiment, breakaway power connections 505 and 515 connect external battery 145' directly to system controller 125' housing and no power leads or cables are required.

Breakaway power connections minimize trauma to the exit site if system controller 125' is dropped, external battery 145' or power adapter 155 is forcibly pulled from system controller 125', or other stress is applied to one or more of the individual VAS components. At a predetermined force, the breakaway power connections between the VAS components separate (i.e., decouple) such that only the weight of system controller 125' acts on drive line 115' and the exit site. Stress on drive line 115' often directly leads to stress at the exit site where drive line 115' enters the patient. Lowering the risk of trauma experienced by the exit site lowers the potential risk for infection to the patient.

In one embodiment, the breakaway power connections use passive or active (e.g., electromagnetic) magnets to control the sequence of devices that disconnect when external stress is applied to any of the coupled VAS components. For example, a patient may get a line or component caught on an object while walking, and the breakaway power connection ensures the external battery separates before causing external stress to the exit site. In one embodiment, the passive or active magnets further comprise secondary mechanical features to restrain the transverse movements of the power connections. In other embodiments, the breakaway power connection is a slide rail mechanical connection or a combination of all previously mentioned connections. In one embodiment, system controller 125' automatically switches to internal power when an external source of power (e.g., external battery 145' or power adapter 155) is lost or has a fault condition.

Figure 22:
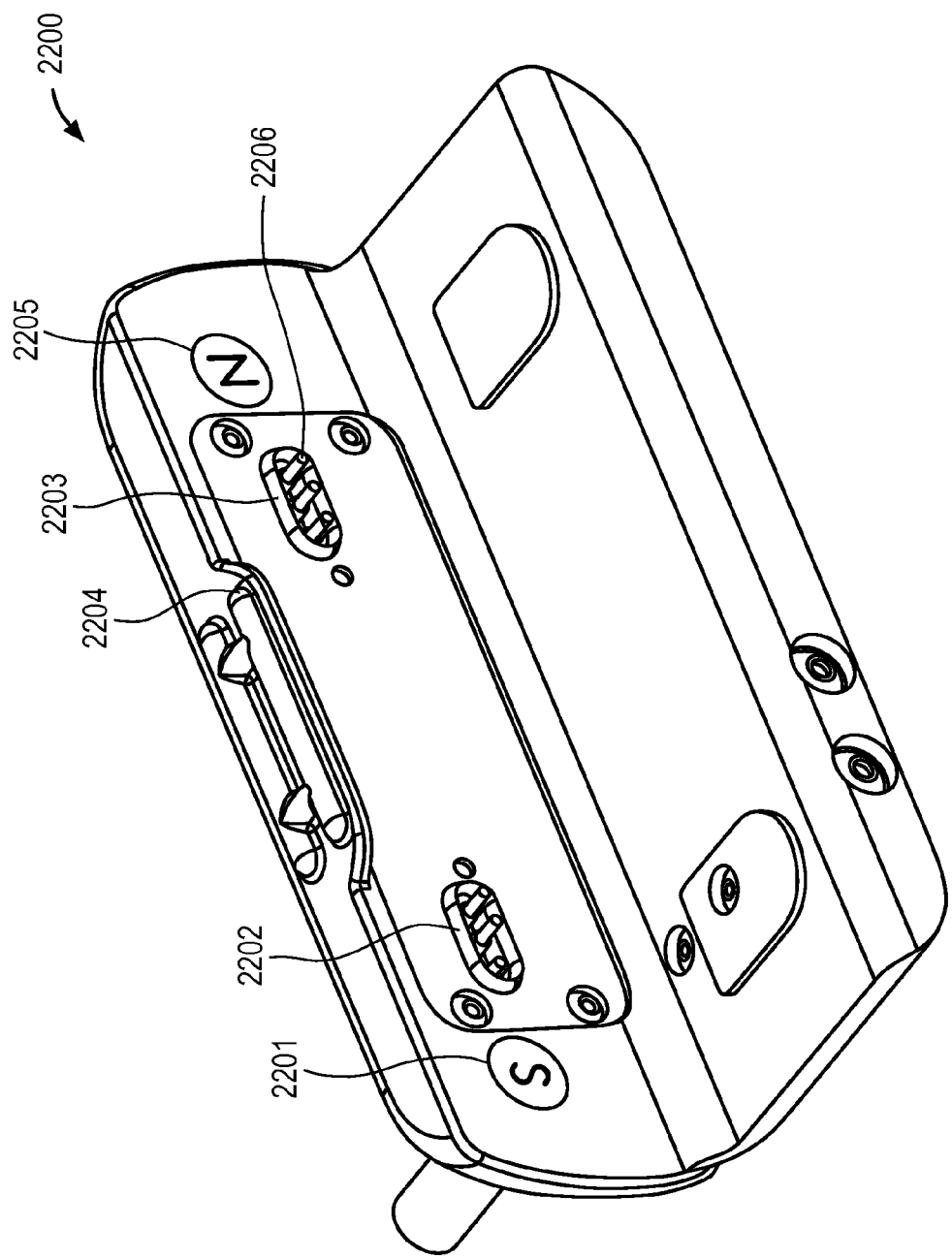
FIG. 22 is a perspective view illustrating one embodiment of a power adapter having magnetic connections, and power connections.
Figure 23:
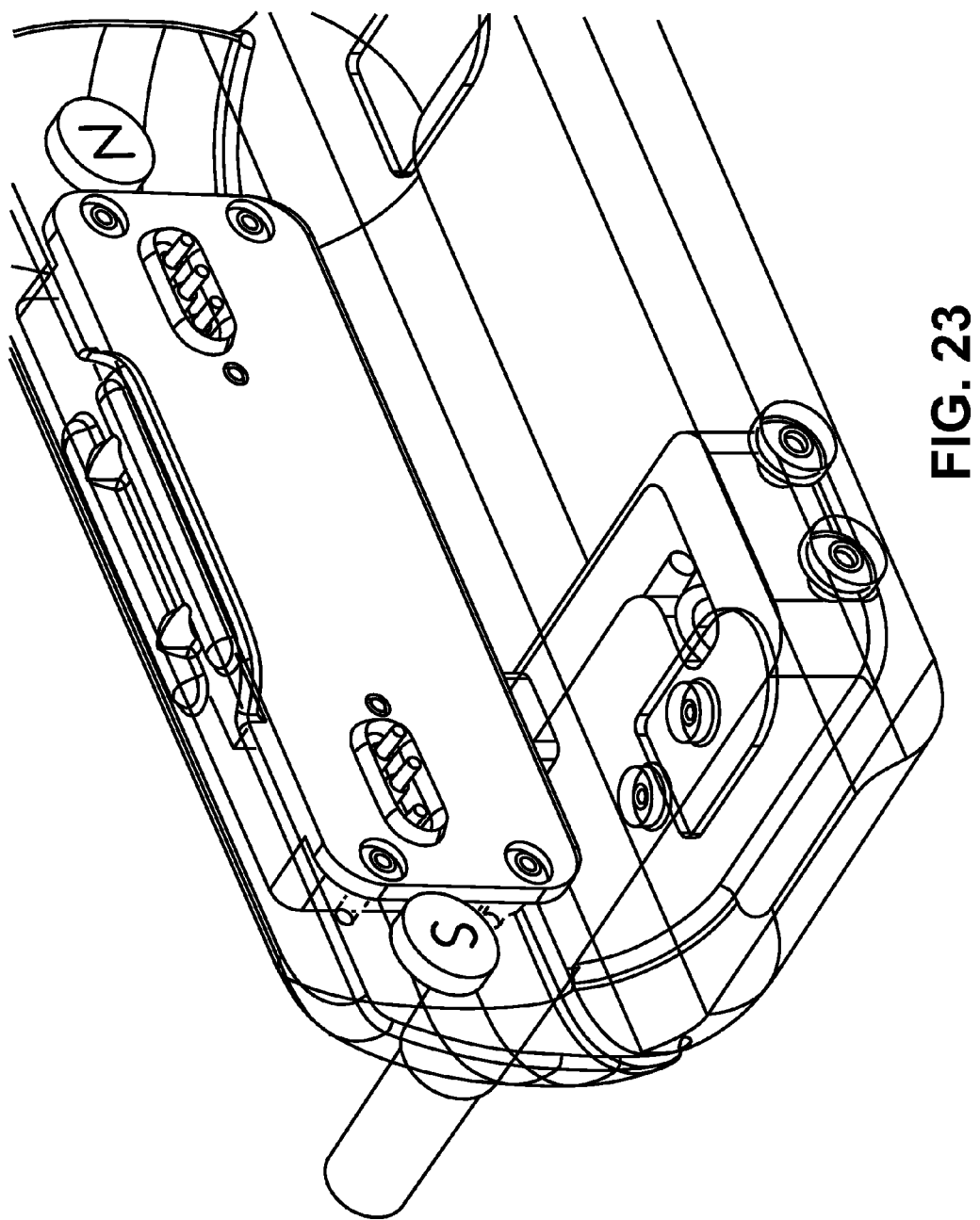
FIG. 23 is a partial perspective view illustrating one embodiment of a power adapter having magnetic connections, and power connections.
Figure 24:
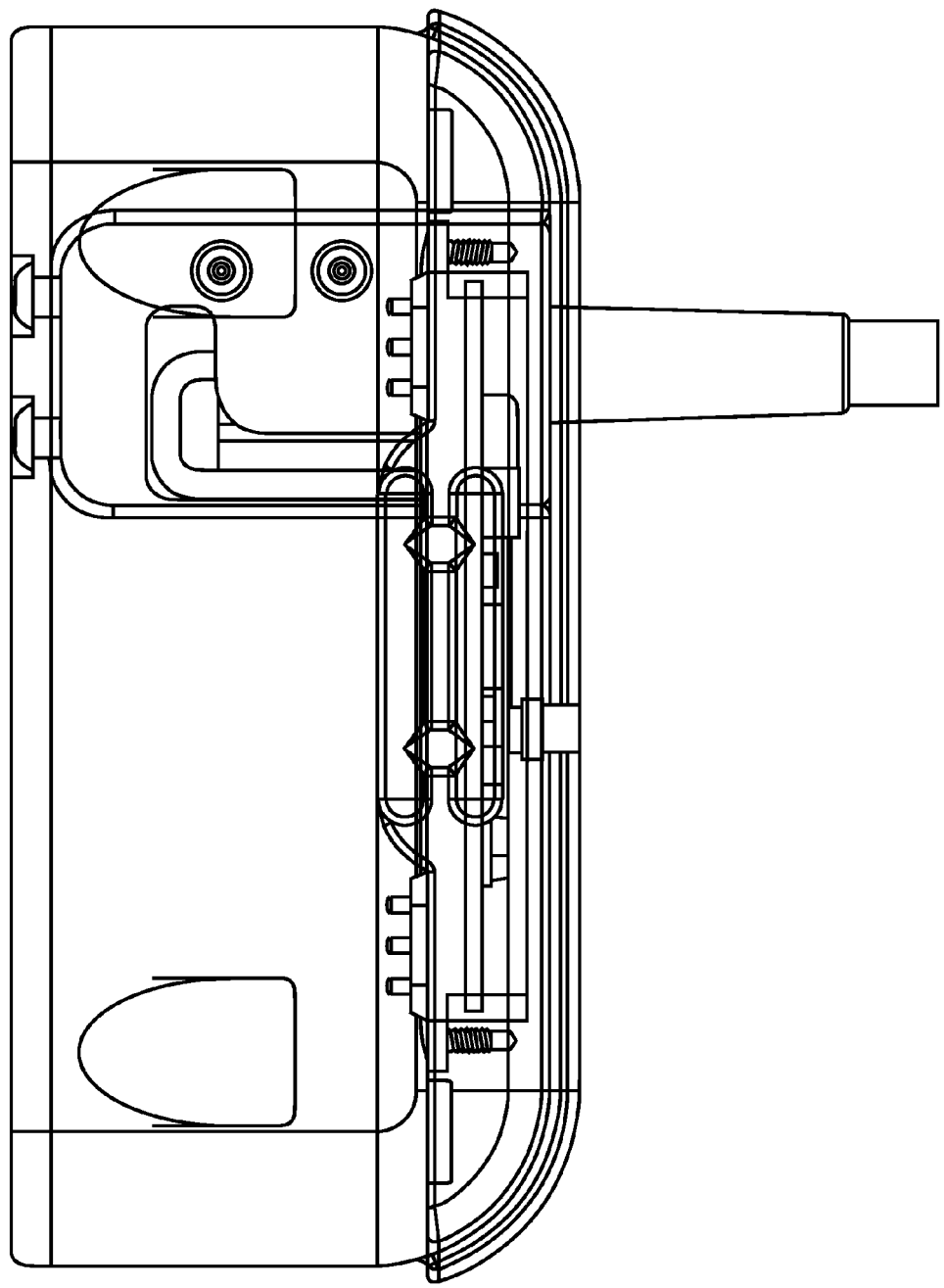
FIG. 24 is a projected illustrating one embodiment of a power adapter having magnetic connections, and power connections.
Figure 25:
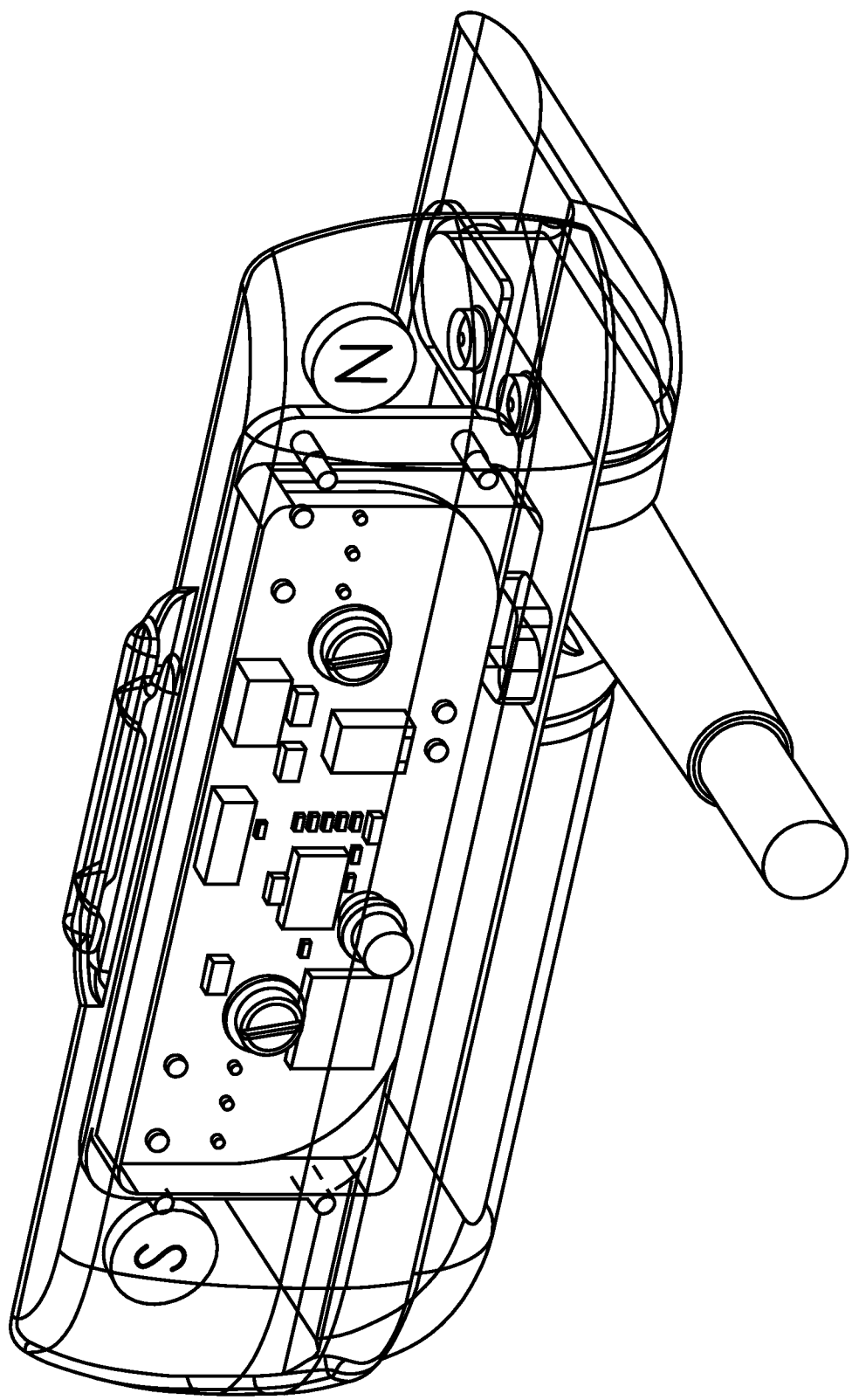
FIG. 25 is a partial perspective view illustrating one embodiment of a power adapter having magnetic connections, and power connections.
Figure 26:
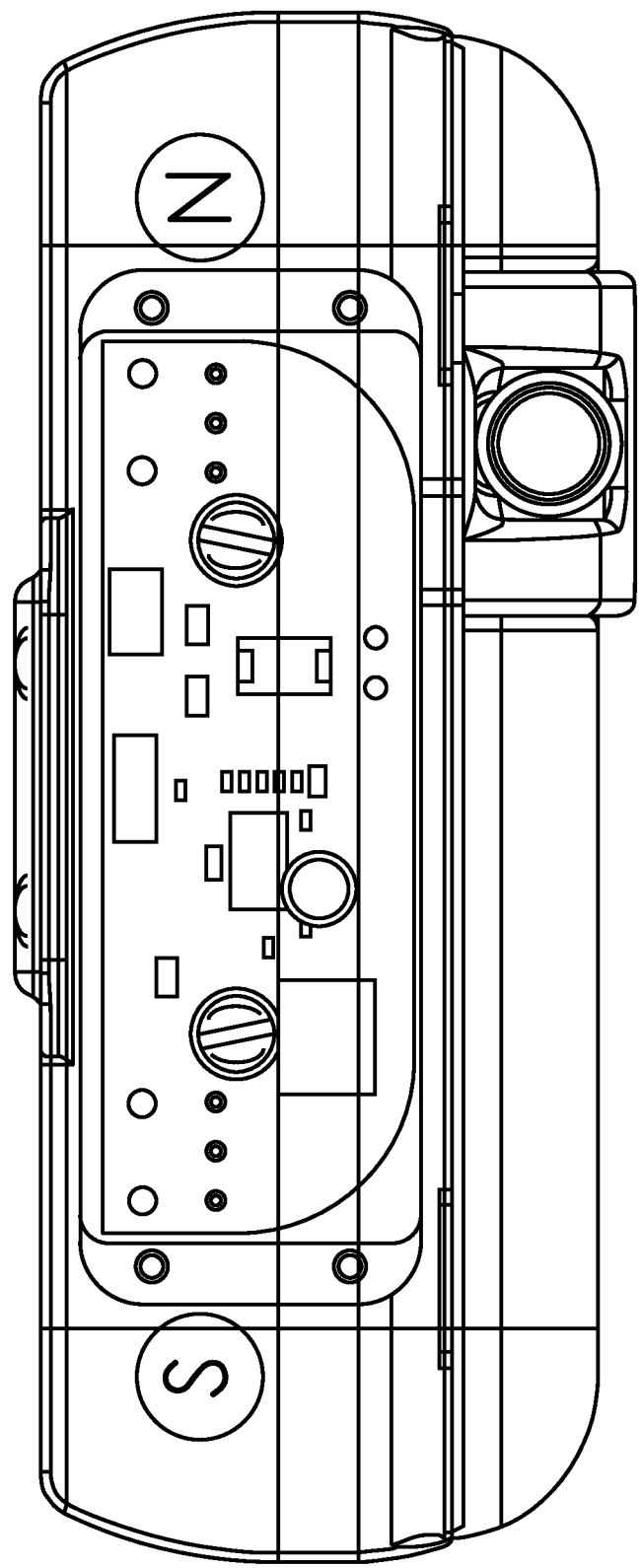
FIG. 26 is a projected view illustrating one embodiment of a power adapter having magnetic connections, and power connections.

FIG. 22 illustrates a perspective view of one embodiment of a power adapter 2200 with breakaway power connections. In one embodiment, power adapter 2200 has one or more magnets (e.g., magnet 2201 and 2205) that can be mechanically coupled to magnets in system controller 125. In one embodiment, the one or more magnets (e.g., magnet 2201 and 2205) have different (e.g., opposite) polarity relative to other magnets in power adapter 2200. For example, magnet 2201 can have a first polarity (e.g., South) and magnet 2205 can have a reverse polarity (e.g., North), or vice versa. In one embodiment, the one or more magnets are separate physical connections from power connections 2202 and 2203 that provide (e.g., conduct) power to system controller 125 or external battery 145. In other embodiments, a magnet is integrated into the power connection (e.g., integrated into power connection 2202 or 2203). In one embodiment, system controller 125 and external battery 145 have similar or identical components to allow for coupling to power adapter 2200. In one embodiment, power adapter 2200 and system controller 125 have mechanical components (e.g., slide rails) to align the connections (e.g., power pins 2206) and magnets to a targeted point of contact. In one embodiment, power adapter 2200 has an integrated overhang or lip 2204 to cover the infrared port of the system controller when the system controller and power adapter are mechanically coupled together.

In one embodiment, the force required to decouple a breakaway power connection is predetermined such that an axial loading event applied to both external battery 145' and power adapter 155 cause power adapter 155 to decouple first. Pre-configuring the force required for each breakaway connection allows system controller 125' to exert minimal force on the percutaneous cable while also providing a predetermined breakaway sequence. In one embodiment, external battery 145' is coupled to power adapter 155 as well as system controller 125'.

In one embodiment, when more than two devices (e.g., system controller, battery, and power adapter) are connected together, an ordered breakaway event is possible. For example, in the event of a force (e.g., a physical force, mechanical force, pull or tug) on drive line 115' or power adapter 155 cable, power adapter 155 is the first device to decouple from a component in the VAS. If there is further or increased force on drive line 115', external battery 145' detaches from system controller 125'. In one embodiment, the magnet strength in each breakaway connection is predetermined to enforce a specific breakaway order or sequence. For example, the magnets coupling power adapter 155 to system controller 125 can be less magnetic (e.g., lower strength/attraction), than the magnets coupling external battery 145 and system controller 125.

In one embodiment, one or more of the magnets is an electromagnet. In one embodiment, an electromagnet is integrated into the power connection used for coupling and decoupling power adapter 155 (AC or DC) to system controller 125. In one embodiment, the same power connection with an integrated electromagnet is also used to couple power adapter 155 to external battery 145. In one embodiment, as power adapter 155 or external battery 145 approaches system controller 125, a magnetically activated relay in power adapter 155 or external battery 145 is triggered by a specially located magnet. In one embodiment, the specially located magnet is in one or more of system controller 125, external battery pack 145, and power adapter 155. In one embodiment, activating/triggering the magnetic switch also activates/triggers the electromagnet at one or more of the connections on system controller 125, external battery 145 or power adapter 155 (e.g., an AC or DC power adapter). In one embodiment, activating/triggering the electromagnet increases the attractive magnetic force between the one or more system components (e.g., power adapter, external battery and system controller). Increasing the electromagnetic force increases the pull between components and also helps in aligning the coupled components. In one embodiment, the electromagnet is powered briefly to reduce power consumption.

In one embodiment, when the magnetic switch is deactivated/disengaged (e.g., because power adapter 155 or external battery 145 is no longer in close proximity to system controller 125) the electromagnet reverses current, negating the magnetic field from the internal magnets. Negating the magnetic field facilitates the breakaway process of the connected components when the components are subjected to a force (e.g., cord pull or excessive twisting).

In one embodiment, the mechanical features facilitating the coupling of system 125 prevents transverse motion or shearing between system controller 125 and other connected devices and does not prevent or restrain the axial position of connected modules.

Redundant and Flexible Alert Delivery

In one embodiment, system controller 125 implements one or more types of alarms (e.g., visual, audible, and/or vibratory). Alarm data associated with an alarm can be one or more of a hazard, alert, notification or event. Alarms can be represented on touch screen 330 as one or more of visual text, icons, images, video, charts, and graphs. In one embodiment, the alarms on system controller 125 are mirrored (duplicated) on external battery touch screen 330. Visual alarm information on external battery touch screen 330 can also include text descriptions of the alarm in a choice of one or more languages. Alarm information can also include recommendations to fix the cause of the alarm, or ways to quiet/disable an alarm. For example, display 240 can present a recommendation for the user of the device to contact a technician or recommendations for servicing (e.g., the connections on system controller 125 have an error, or the infrared window needs cleaning). In one embodiment, alarms are displayed as text messages, lights or icons displayed on system controller 125. In one embodiment, the vibratory alerts supplement the audible and visual alarms for hazards and advisories. In one embodiment, system controller 125 and external battery pack 145 store alarm history in memory 205 and memory 305, respectively.

In one embodiment, system controller 125 sends alerts or status information to external device 270 and/or external battery 145. In one embodiment, external battery 145 and/or an external device 270 provides real time mirroring of alerts provided by system controller 125. As used herein, mirroring of an alarm duplicates the alarm data provided by system controller 125 to another external device 270 and/or external battery 145. For example, if pump 110 error is detected by system controller 125, an alarm on system controller 125 is set on system controller 125 as well as on external device 270 and/or external battery 145. Mirroring of alarms insures that important system information is conveyed to the patient despite a failure of the alarm output on one of the system components. For example, if an alarm sounds on system controller 125 when the speed of the motor reaches an unacceptably low level, a representation of the alarm data is displayed on system controller 125 as another representation of the alarm data is displayed on external battery 145. In another example, system controller 125 can provide one or more alarms to notify the patient of the low battery level of internal battery 230. In one embodiment, alarms on system controller 125 are represented by one or more LEDs.

In one embodiment, external battery 145 also implements one or more alarms (e.g., visual, audible, and vibratory) and also provides alerts for battery 320 as well as system controller's internal battery 230. In other embodiments, external battery 145 monitors its own battery level and can provide an alarm based on an independent determination of battery status separate from system controller 125.

In one embodiment, alarm 245 on system controller 125 is the primary alarm system to provide alarm notification at all times regardless of the presence of external battery 145 and alarm 335. In other embodiments, alarm 245 on system controller 125 is not activated while alarm 335 on external battery 145 is active. In one embodiment, an alarm occurs only on external battery 145 when the alarm is only associated with integrated battery 320. In one embodiment, alarms associated with integrated battery 320 occur when external battery 145 is decoupled from system controller 125. Alarms can also occur during the coupling or decoupling of external battery 145 to/from system controller 125 or power adapter 155. In one embodiment, external battery 145 alarm 335 receives alarm data from system controller 125 by an infrared communications link. Alarm data can be used to synchronize timing and logs associated with alarms on system controller 125 and external battery 145.

In one embodiment a fall or impact recorded by an accelerometer integrated into system controller 125 or external battery 145 is recorded and represented as an alarm. A fall or impact can also be followed by a series of questions to the user displayed on the external battery touch screen.

External Battery and System Controller Infrared Communication

In one embodiment, system controller 125 communicates with external battery 145 and/or other detachable device using an infrared communications link (e.g., IrDA). Implementing an infrared communications link to connect system controller 125 and external battery 145 provides for robust wireless communications between system controller 125 and external battery pack 145. Infrared communication does not occupy bandwidth in frequency ranges regulated by the Federal Communications Commission (FCC). Furthermore, using infrared reduces or eliminates errors and failures associated with other forms of wireless communication (e.g., electrostatic discharge, electromagnetic interference, or other naturally occurring electromagnetic phenomenon on the physical communications hardware). In addition, an infrared port, such as infrared port 510 window is easily cleaned and maintained by untrained operators and allows for a waterproof system controller 125. Incorporating an infrared port as opposed to an Ethernet or other exposed electrical ports facilitates a waterproof enclosure design while retaining robust mechanical design (i.e., fewer mechanical parts; no electromechanical connector). Through sealing of the infrared port and other novel features described in this application (e.g., intelligent power disconnects), it is possible to manufacture system controller 125 such that it is completely waterproof and meets IP68 (Ingress Protection Rating) standards. In other embodiments, external battery 145 also contains an infrared port and is water resistant.

In one embodiment, when system controller 125 and external battery pack 145 are in close proximity to each other, a switch is triggered or activated in system controller 125. In one embodiment, the switch is a magnetic switch (e.g., a reed switch or Hall effect switch) which can be considered to be a form of a proximity sensor. In other embodiments, the magnetic switch is located in external battery pack 145. Upon detecting that the magnetic switch is triggered, external battery pack 145 initiates communications with the system controller 125. In other embodiments, upon detecting that the magnetic switch is triggered, system controller 125 initiates communication with external battery pack 145. In one embodiment, infrared communication is used to link external battery 145 and system controller 125. In one embodiment, a user can initiate and/or acknowledge infrared data links and transfers with touch screen 330 on external battery 145. For example, to connect system controller 125 to a base station, an icon or representation of initiating a connection is provided on touch screen 330. In one embodiment, no pump controls are available on touch screen 330 in order to separate the most important functions of system controller 125 from external influence.

Figure 7:
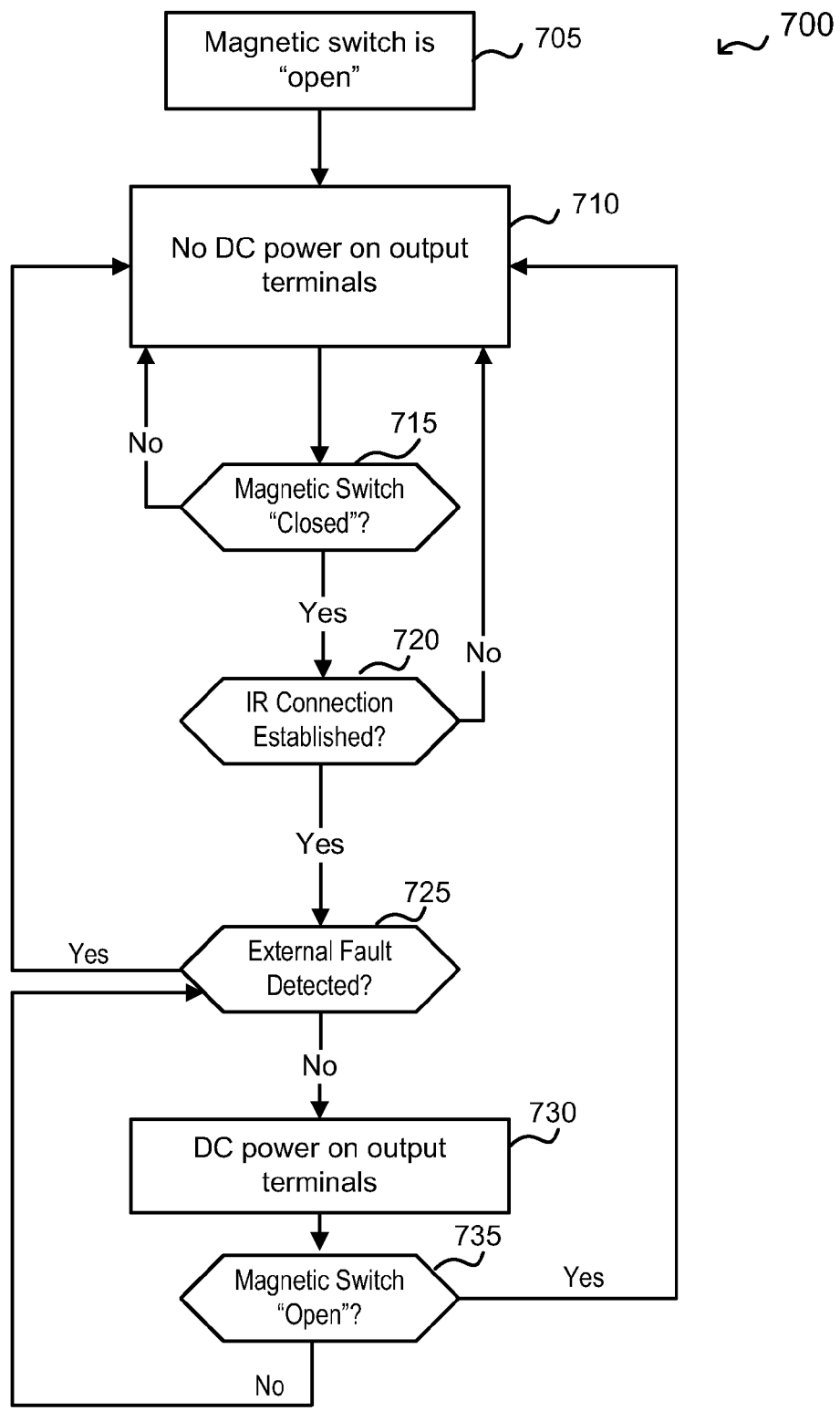
FIG. 7 is a flow chart illustrating a method for providing power to a set of output terminals.

FIG. 7 is a flow chart illustrating an exemplary method 700 for connecting external battery 145 to system controller 125. For example, method 700 may be performed by external battery 145 and system controller 125. For the sake of simplicity, it is assumed that method 700 is performed by system controller 125.

At block 705, the magnetic switch (or other proximity sensor) in system controller 125 is "open" and has not been triggered by any close proximity magnet (or other trigger such as light if a light sensor is used).

At block 710, the output power terminals (e.g., output connections 505 and 515) of system controller 125 are decoupled such that they cannot receive or send power.

At block 715, system controller 125 determines whether the magnetic switch is in a "closed" state. For example, the proximity of external battery 145 triggers the magnetic switch of system controller 125 so that the switch enters the "closed" state. If the switch remains open, the method 700 returns to block 710 and no power is output to the terminals.

At block 720, system controller 125 determines whether an infrared connection to external battery 145 is established. If no infrared connection is detected, the output power terminals remain decoupled.

At block 725, system controller 125 determines that an infrared connection exists with external battery 145 and system controller 125 determines whether an external fault is detected. If an external fault is detected, method 700 returns to block 710 and no power is output to the terminals.

At block 730, system controller 125 determines no external fault is detected, and allows DC power on the output terminals.

At block 735, system controller checks whether the magnetic switch is "open." If the magnetic switch is "open" method 700 returns to block 710 and no power is output to the terminals. Otherwise, method 700 checks for faults at block 725 and maintains power if no fault is detected.

System controller 125, upon detecting an enabled connected external battery 145, begins a handshaking routine that both identifies itself and allows the external battery 145 to receive and record data from system controller 125. When external battery 145 is separated from system controller 125, the magnetic switch in the external battery 145 is triggered or deactivated and the infrared communications from the external battery 145 is discontinued.

In one embodiment, the frequency range of the infrared communication is between the FCC regulated portion of the RF (radio frequency) spectrum and the visible light spectrum (e.g., approximately within the range of 860 nm-940 nm). At this wavelength, an infrared transmitter transmits data in a point-to-point fashion. Moreover, an infrared transmitter does not emit nor interferes with radio frequency or microwave transmissions. In one embodiment, when system controller 125 and external battery 145 are mechanically coupled the infrared transceiver units are physically shielded from outside interference. In one embodiment, an overhang or lip on external battery 145 or system controller 125 provides physical shielding over the transceiver units. Physically shielding the infrared ports ensures that nearby devices cannot intercept data transmitted between system controller 125 and the external battery 145. Furthermore, shielding the connections prevents external infrared sources, such as heating equipment, from interfering with the communications between system controller 125 and external battery 145. In one embodiment, a window (e.g., polycarbonate tinted material) embedded in the enclosure housing covers the infrared transceivers in external battery 145 and system controller 125. In one embodiment, the window cover protects the transceivers from water, dust, and other potentially damaging elements. In one embodiment, the window is easily cleaned with readily available household or hospital-grade solvent. Untrained users or patients, therefore, are able to easily clean the window to remove any accumulated debris or film.

Users or patients may easily and inadvertently damage electrical contacts or exposed components. Utilizing a wireless communications system eliminates the requirement for electrical contacts or exposed components in the communications system. The flush window cover also allows the enclosure to be made waterproof compliant with IP68 ratings. In one embodiment, the window placed inside the housing enclosure material while it is being manufactured creates a watertight window as the enclosure material forms around it. The window material can be manufactured from plastic that is transparent at infrared frequencies but nearly opaque at visible light frequencies.

Figure 8:
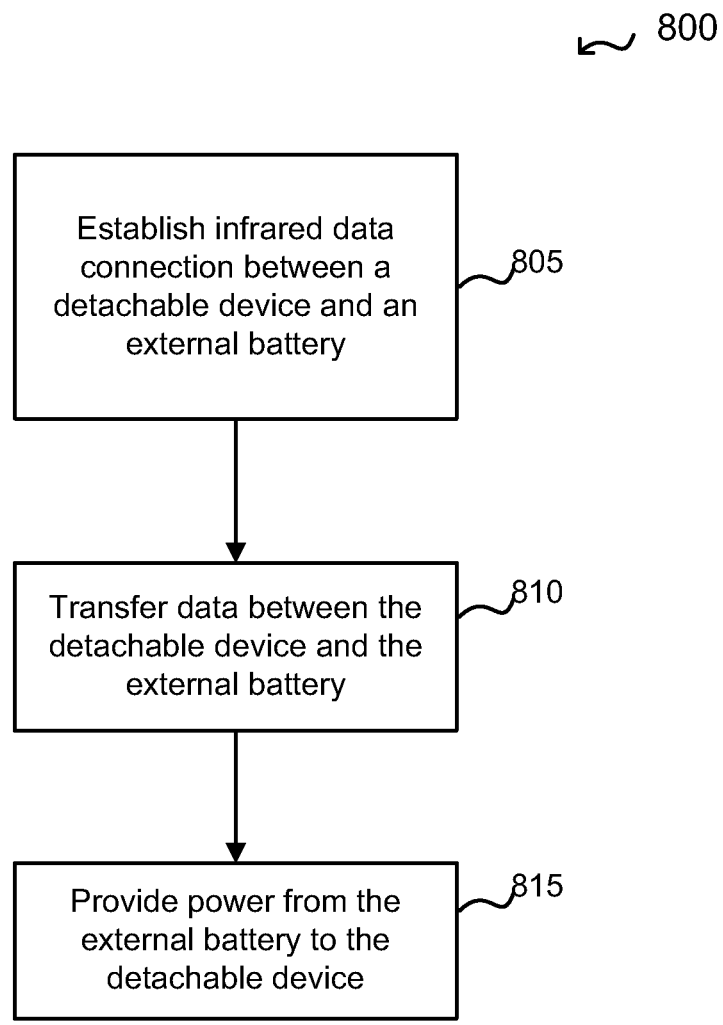
FIG. 8 is a flow chart illustrating a method for providing a data connection and power between an external battery and a detachable device.

FIG. 8 is a flow chart illustrating method 800 for transferring data across an infrared data connection between a first and second detachable device according to one embodiment. In one embodiment, the first detachable device is system controller 125, and the second detachable device is external battery 145 or power adapter 155. For example, method 800 can be performed by the first detachable device. In one embodiment, a proximity sensor (e.g., a magnetic switch) on the first detachable device senses the proximity of the second device. In response, the first detachable device activates (e.g., starts up) an infrared connection between the two devices before the second detachable device is allowed to provide power to the first detachable device.

At block 805, the first detachable device establishes an infrared data connection between the first detachable device and the second detachable device.

At block 810, the first detachable device transfers data, through an infrared connection, between the first detachable device and the second detachable device. In one embodiment, the first detachable device receives the data sent from the second detachable device. In other embodiments, the second detachable device receives data sent from the first detachable device. In yet other embodiments, both the first and second detachable devices send and receive data.

At block 815, the first detachable device enables power from the second detachable device to the first detachable device. In one embodiment, power is only provided after a data connection between the first and second detachable devices has been established.

External batteries and the connections on system controller 125 can sometimes be exposed to outside elements. In one embodiment, system controller 125 and external battery 145 decouple their internal DC power connections, such that no power can flow through the externally exposed power connections. Disconnecting power connections until confirmation of a proximity sensor and an infrared connection insures that accidental power shorting is unlikely to occur. For example, a patient might accidentally connect the power connections 135 and 130 while system controller 125 or external battery 145 touches keys or coins in a pocket or after contact with water. If the exposed connections are exposed to any conductive material a short can occur that can impact vital system components or shock the patient. In one embodiment, requiring one or more of the triggering of a proximity sensor and establishing an infrared connection before coupling the DC power connections greatly reduces the risk of damage or shock to system components and the patient.

Figure 9:
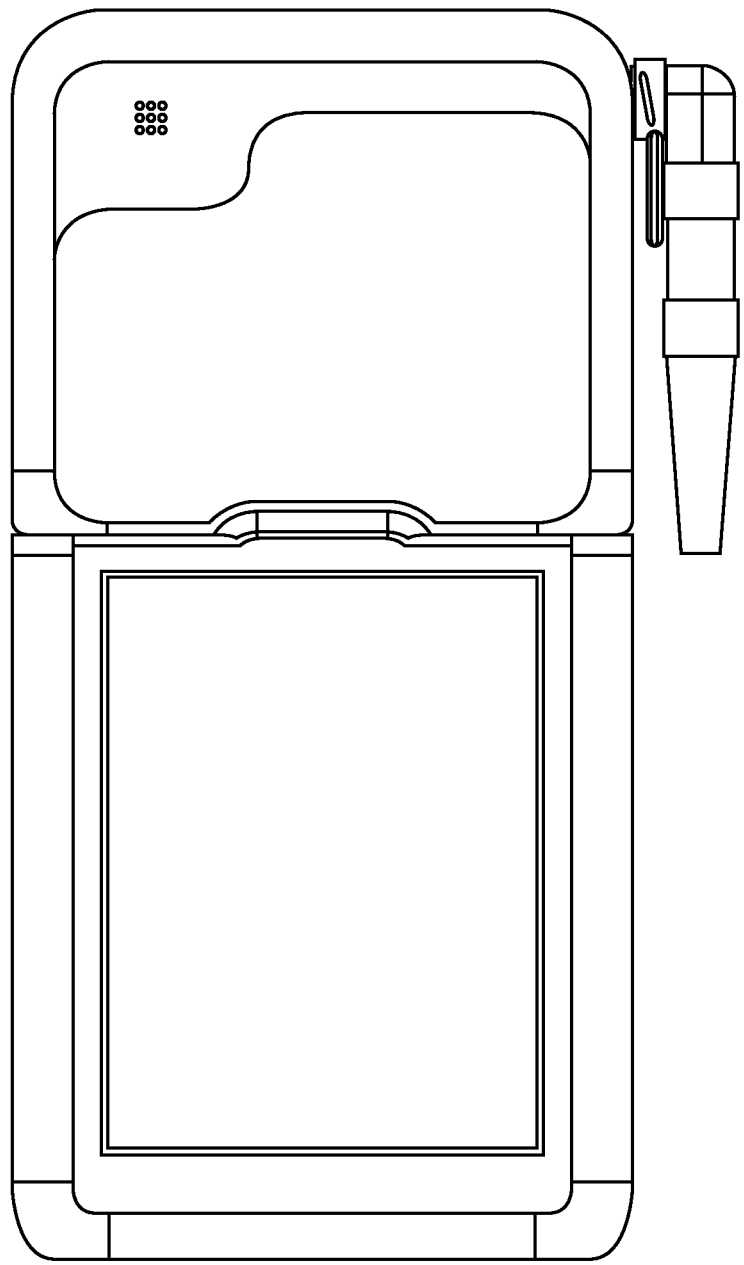
FIG. 9 is a projected view illustrating of one embodiment of a system controller coupled to an external battery and percutaneous lead.
Figure 10:
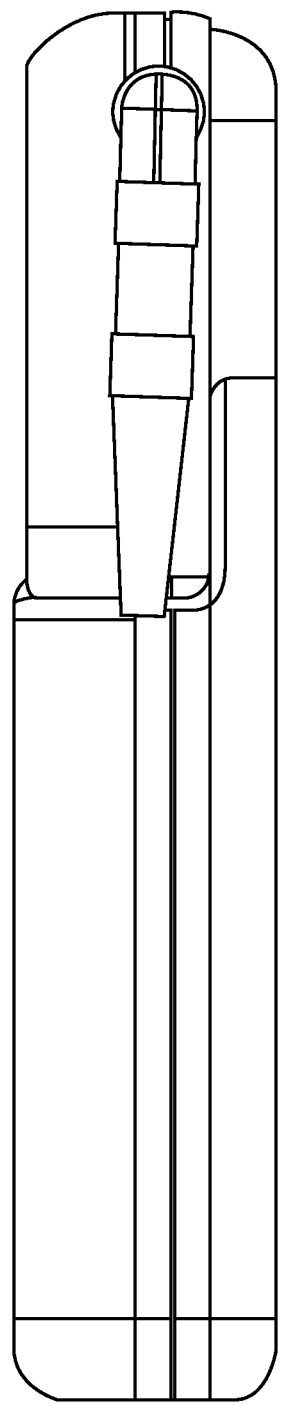
FIG. 10 is a projected view illustrating of one embodiment of a system controller coupled to an external battery and percutaneous lead.
Figure 11:
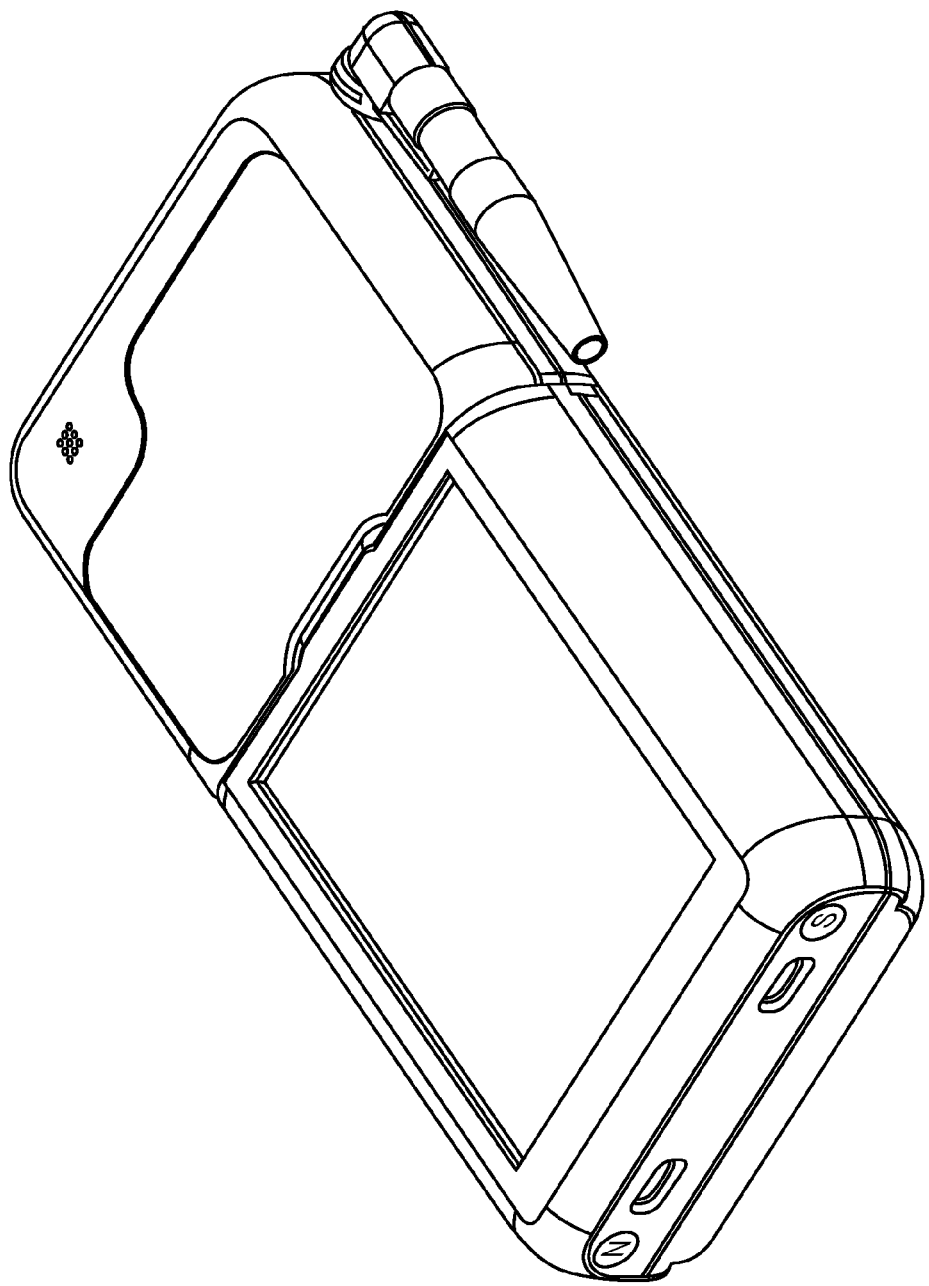
FIG. 11 is a perspective view illustrating of one embodiment of a system controller coupled to an external battery and percutaneous lead.
Figure 12:
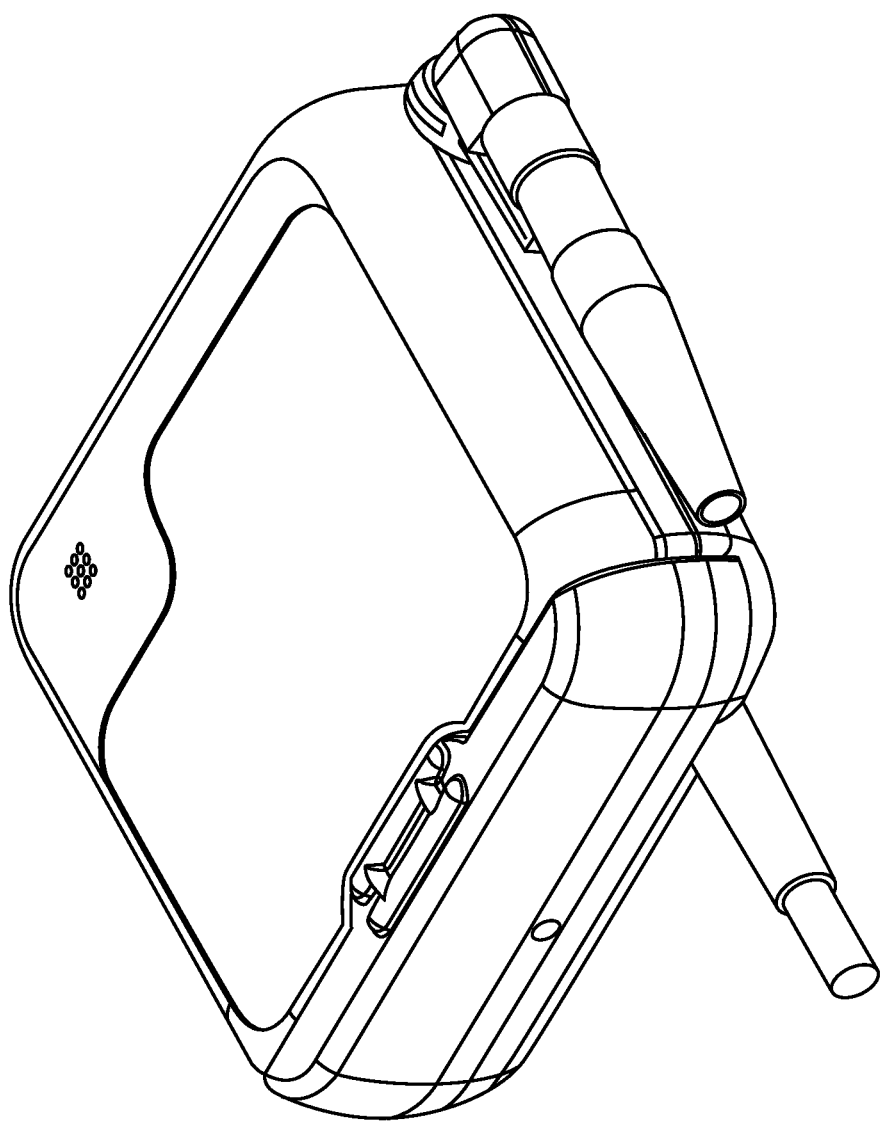
FIG. 12 is a perspective view illustrating of one embodiment of a system controller coupled to a power adapter and percutaneous lead.
Figure 13:
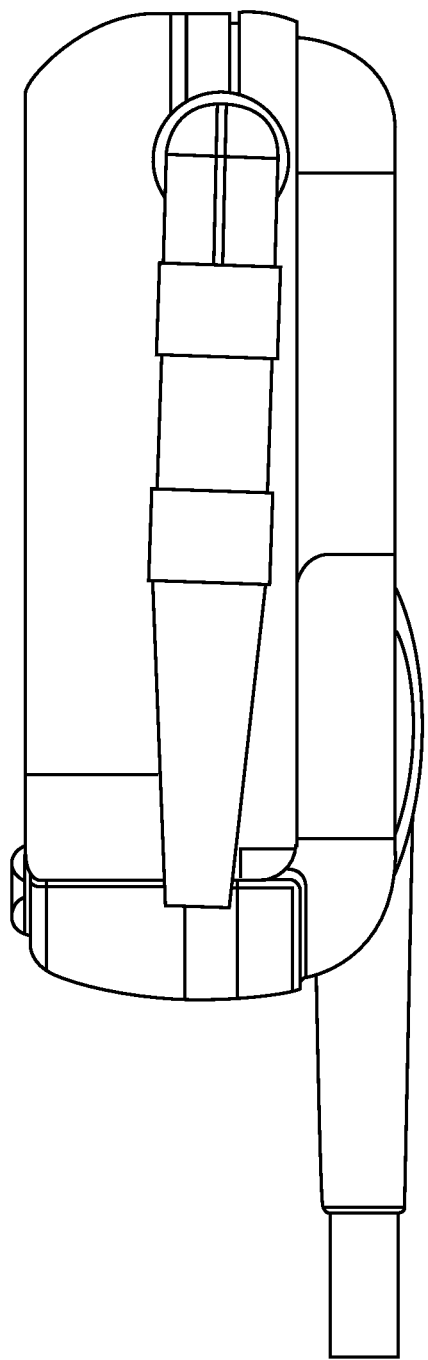
FIG. 13 is a projected view illustrating of one embodiment of a system controller coupled to a power adapter and percutaneous lead.
Figure 14:
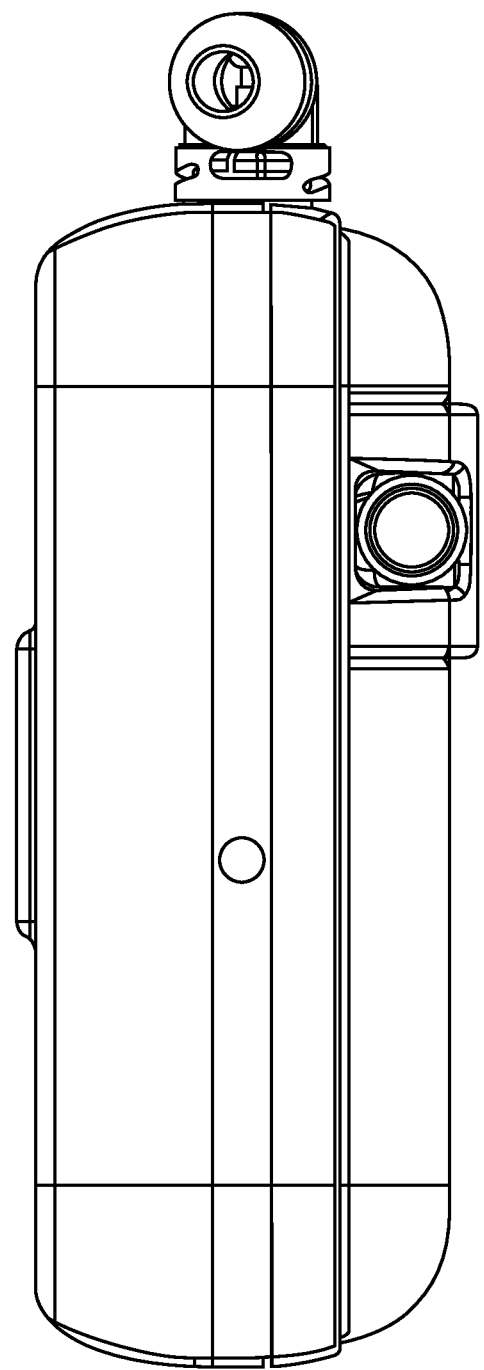
FIG. 14 is a projected view illustrating of one embodiment of a system controller coupled to a power adapter and percutaneous lead.
Figure 15:
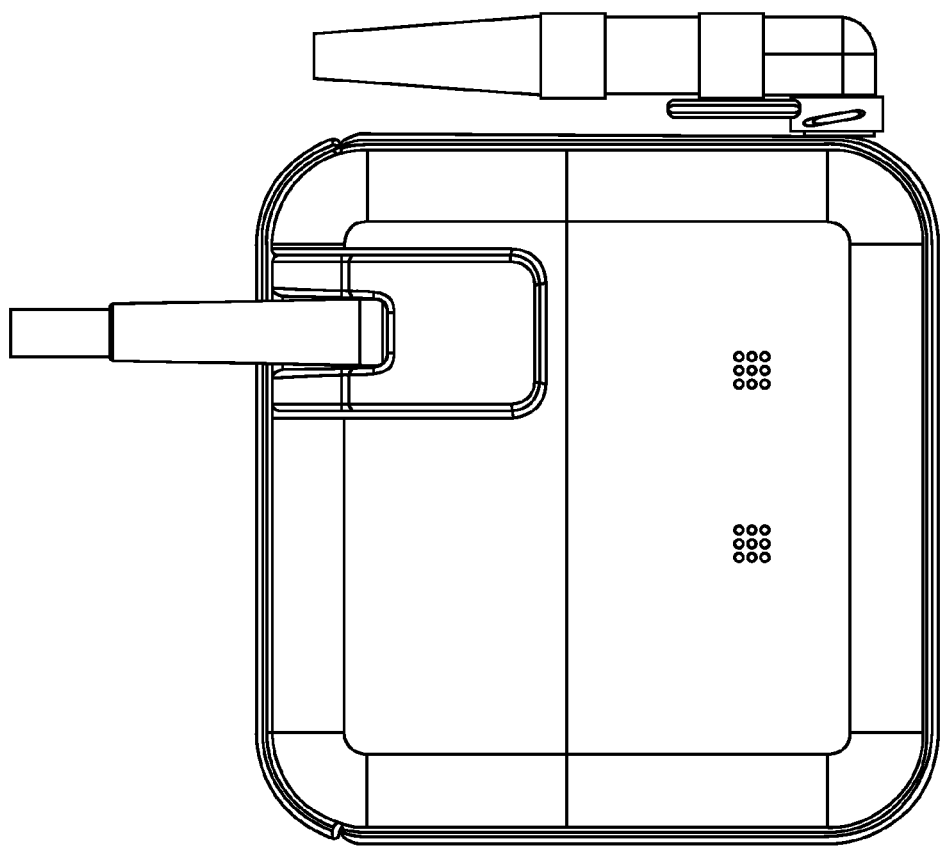
FIG. 15 is a projected view illustrating one embodiment of a system controller coupled to a power adapter and percutaneous lead.
Figure 16:
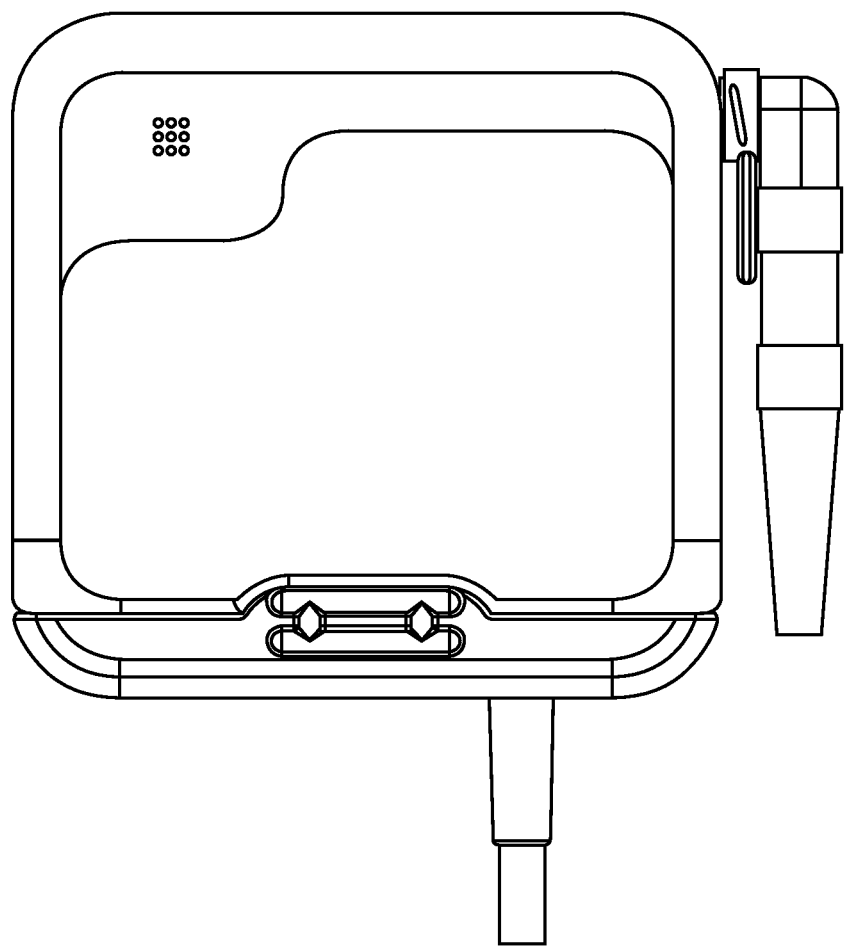
FIG. 16 is a projected view illustrating one embodiment of a system controller coupled to a power adapter and percutaneous lead.
Figure 17:
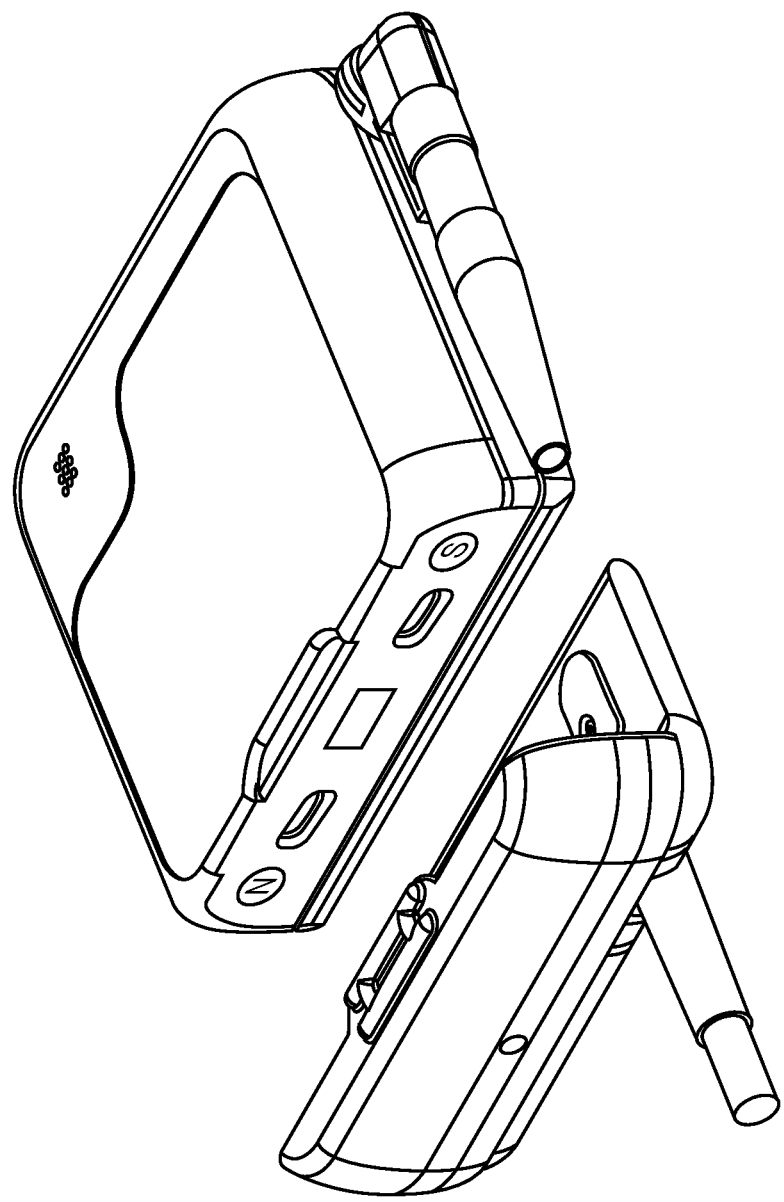
FIG. 17 is a perspective view illustrating one embodiment of a system controller coupled to a percutaneous lead and decoupled from a power adapter.
Figure 19:
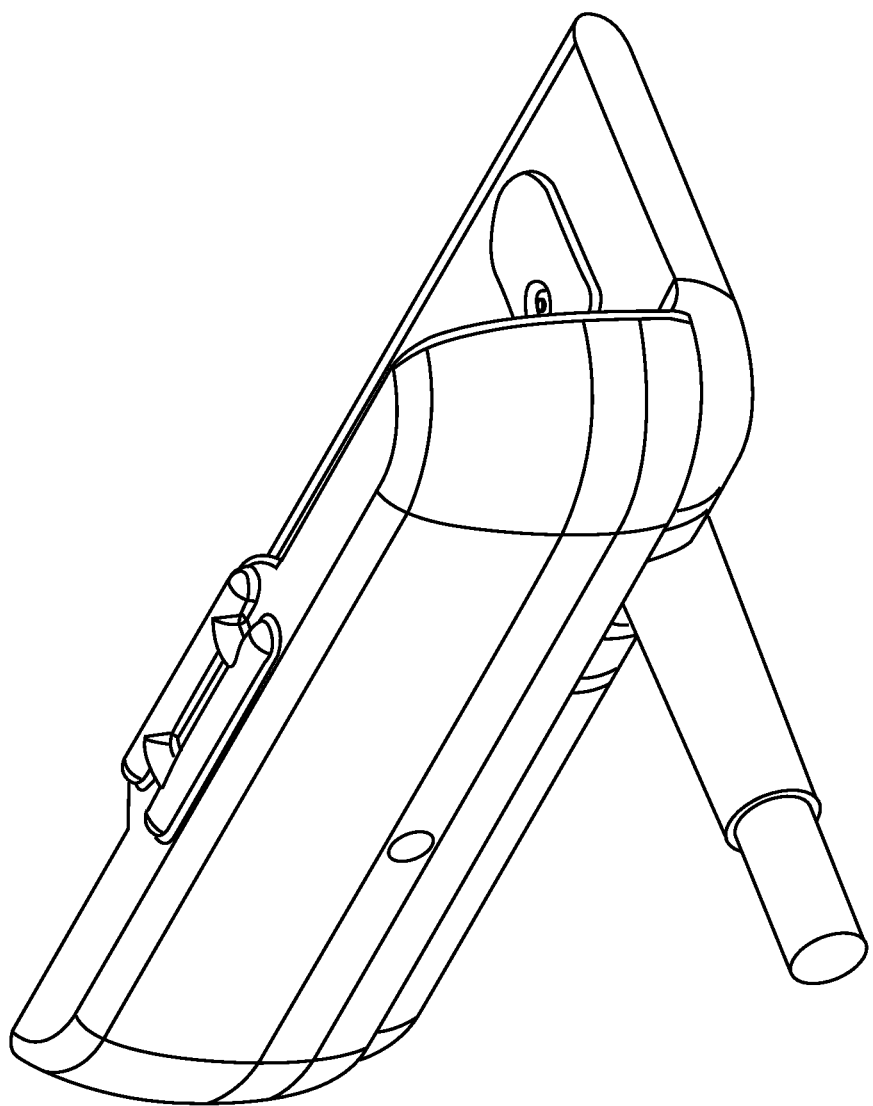
FIG. 19 is a perspective view illustrating one embodiment of a power adapter.
Figure 20:
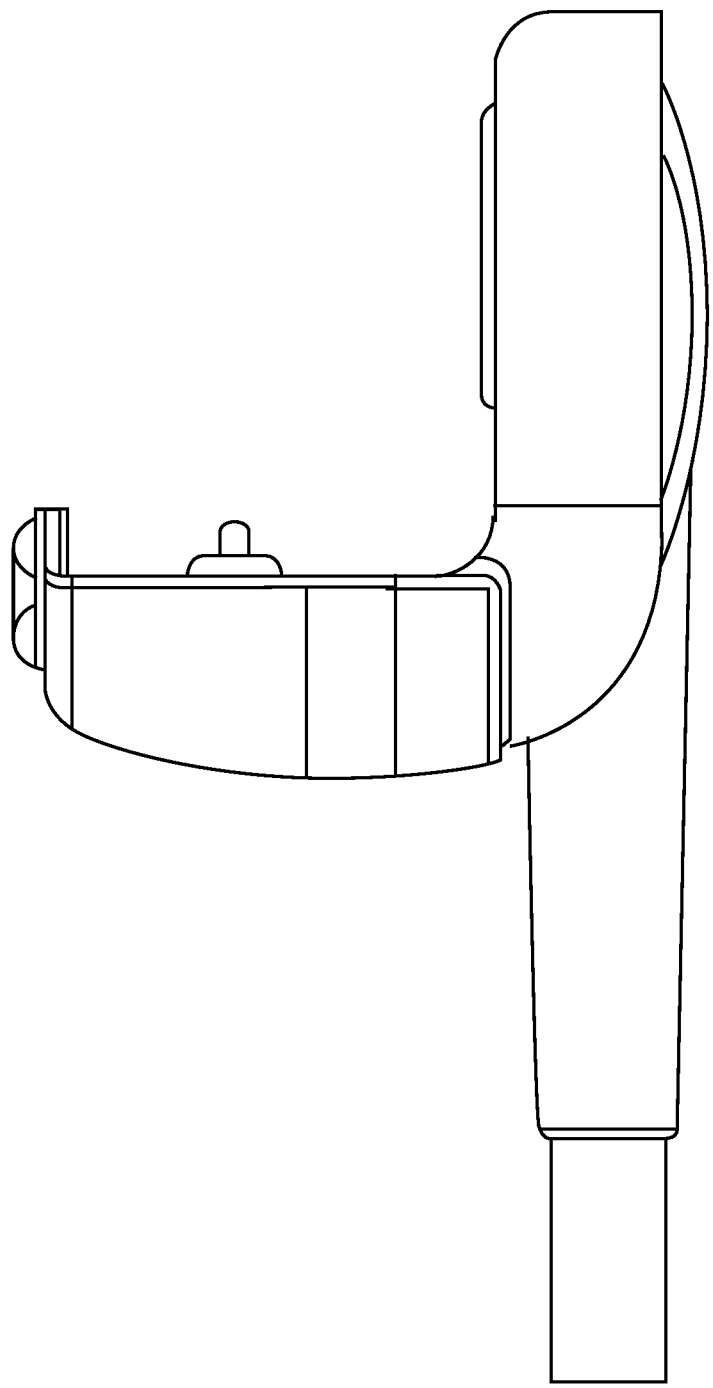
FIG. 20 is a projected view illustrating one embodiment of a power adapter.
Figure 21:
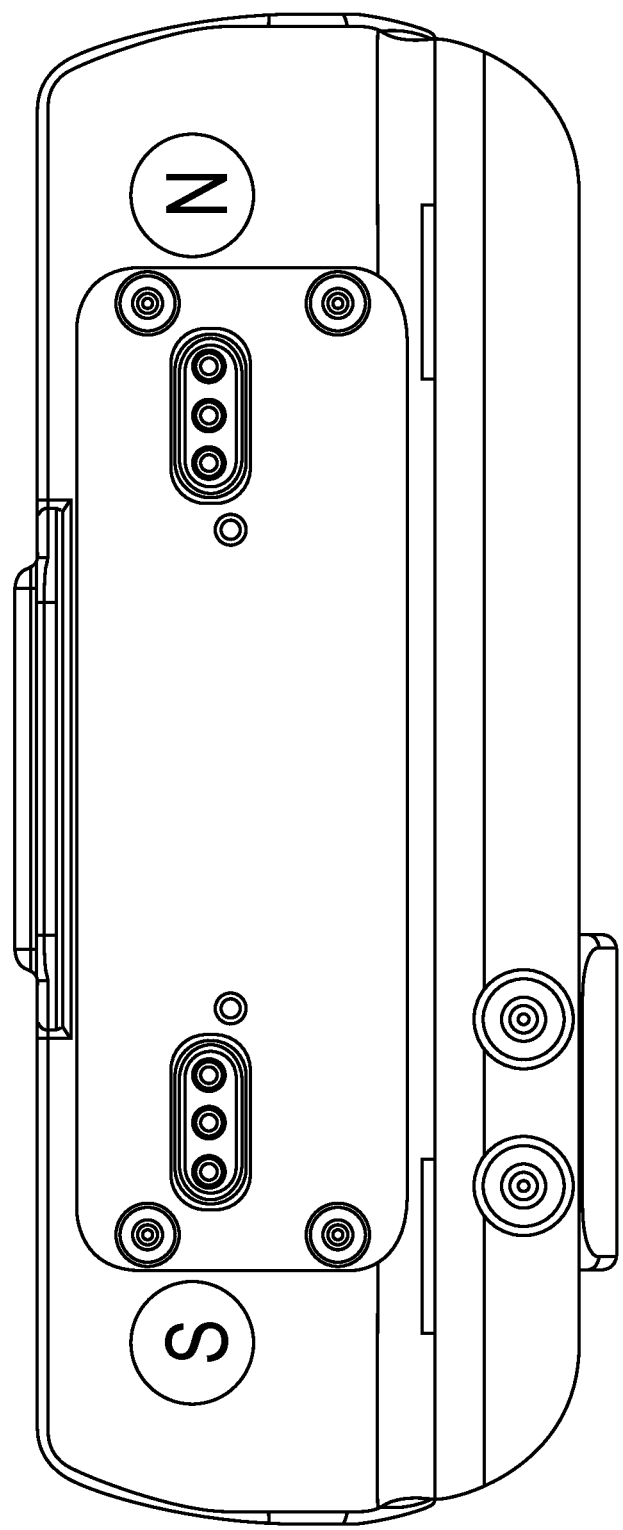
FIG. 21 is a projected view illustrating one embodiment of a power adapter having magnetic connections, and power connections.
Figure 27:
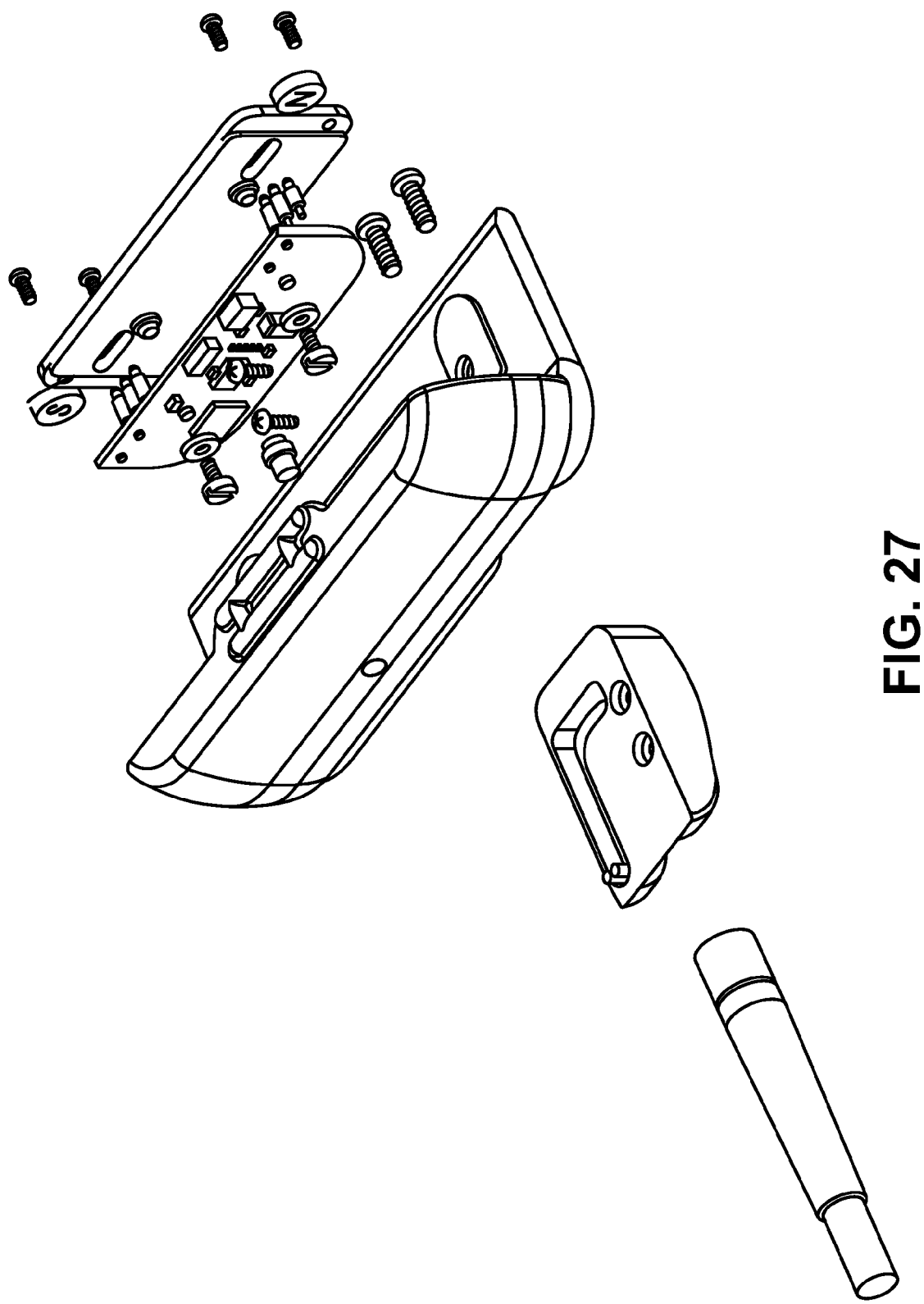
FIG. 27 is an exploded view illustrating one embodiment of a power adapter having magnetic connections, and power connections.
Figure 28:
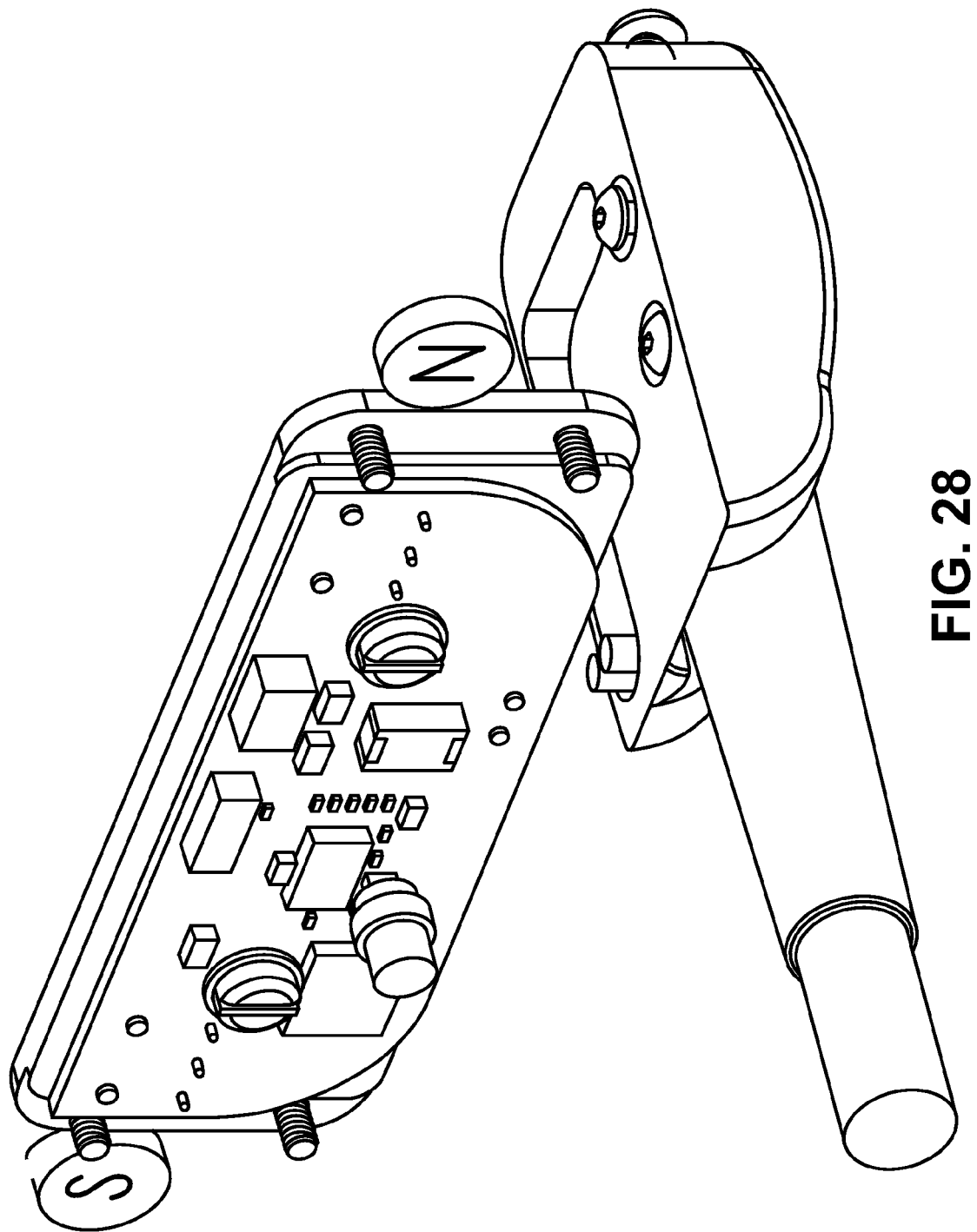
FIG. 28 is an exploded view illustrating one embodiment of a power adapter power cable, power connections and magnets.
Figure 30:
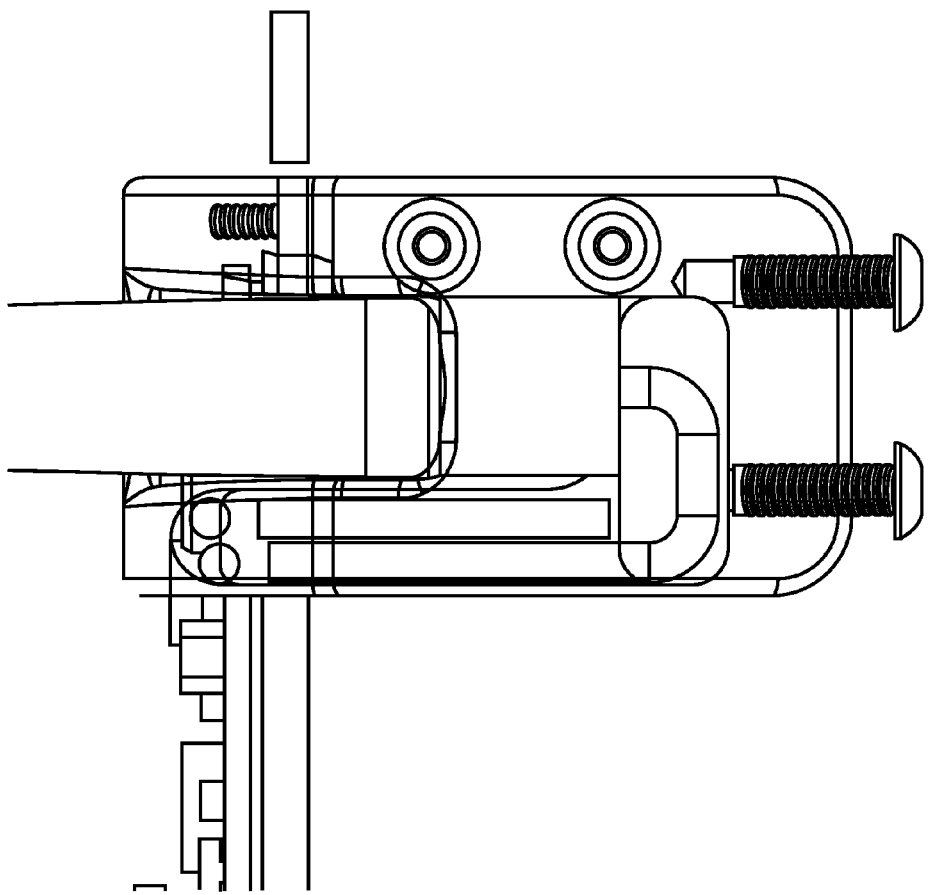
FIG. 30 is a projected view illustrating one embodiment of a power adapter power cable connection.
Figure 31:
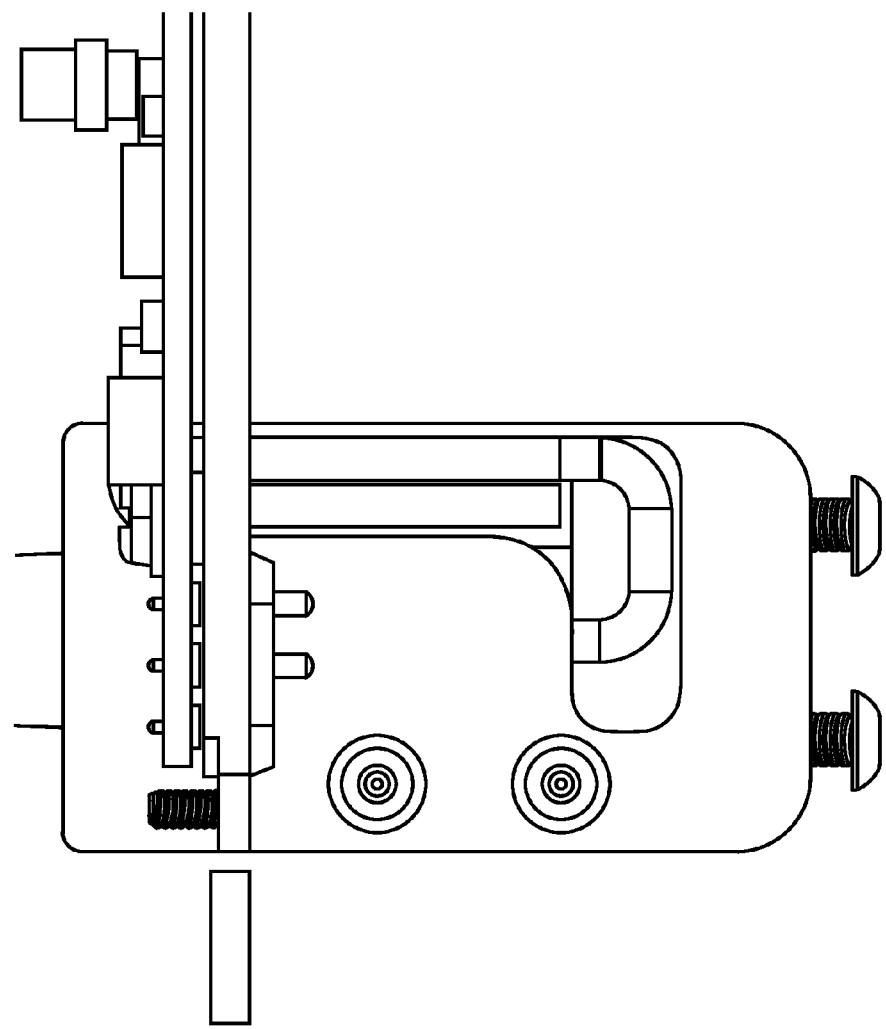
FIG. 31 is a projected view illustrating one embodiment of a power adapter power cable connection.
Figure 32:
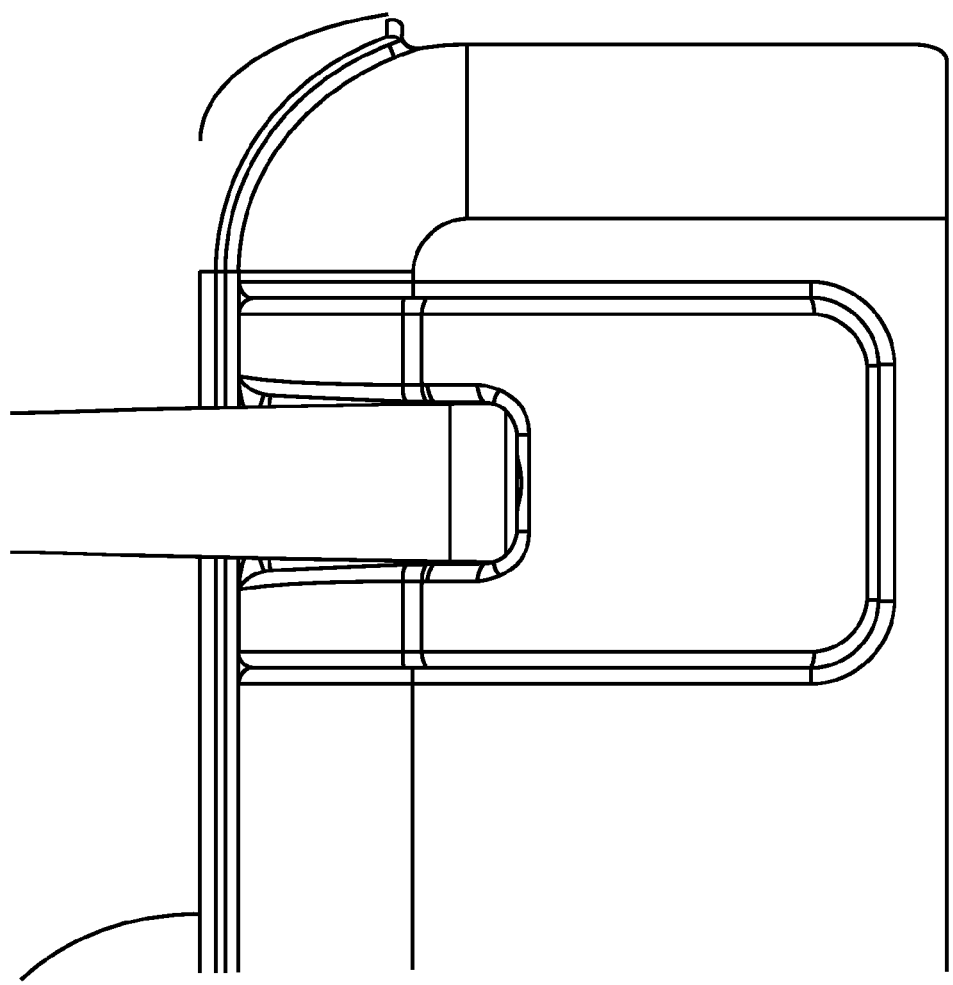
FIG. 32 is a projected view illustrating one embodiment of a power adapter power cable connection.
Figure 33:
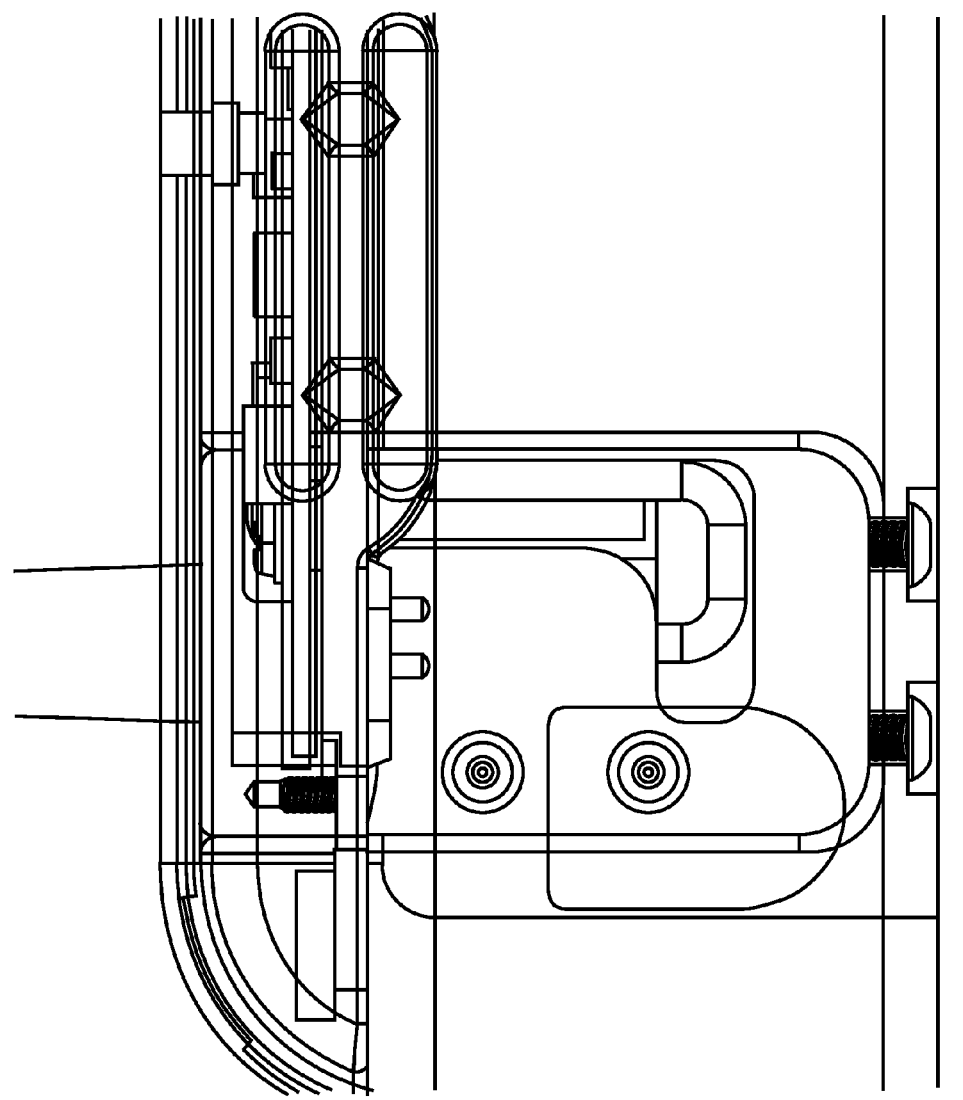
FIG. 33 is a projected view illustrating one embodiment of a power adapter power cable connection.
Figure 34:
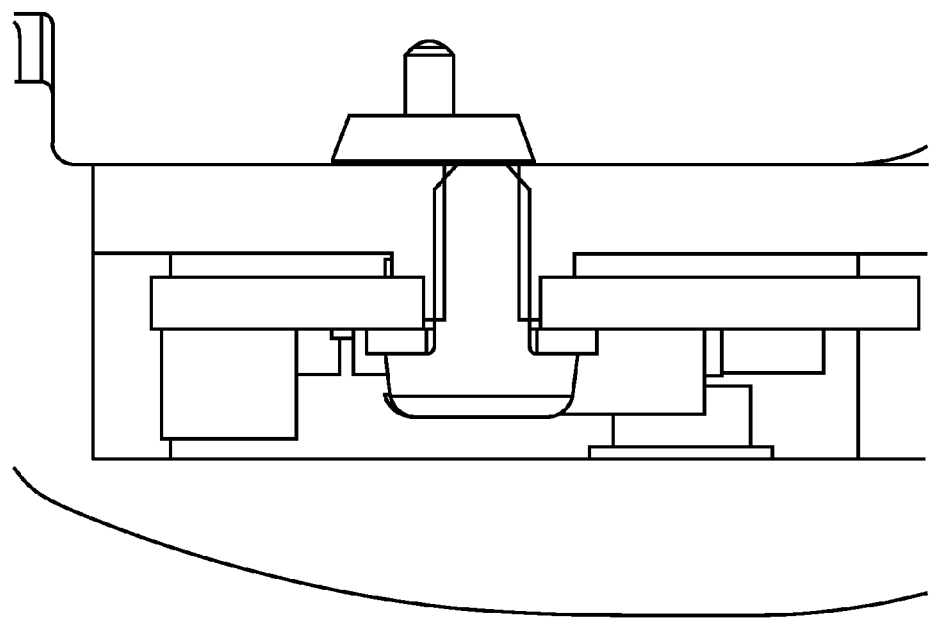
FIG. 34 is a projected view illustrating one embodiment of a power adapter having magnetic connections, and power connections.
Figure 35:
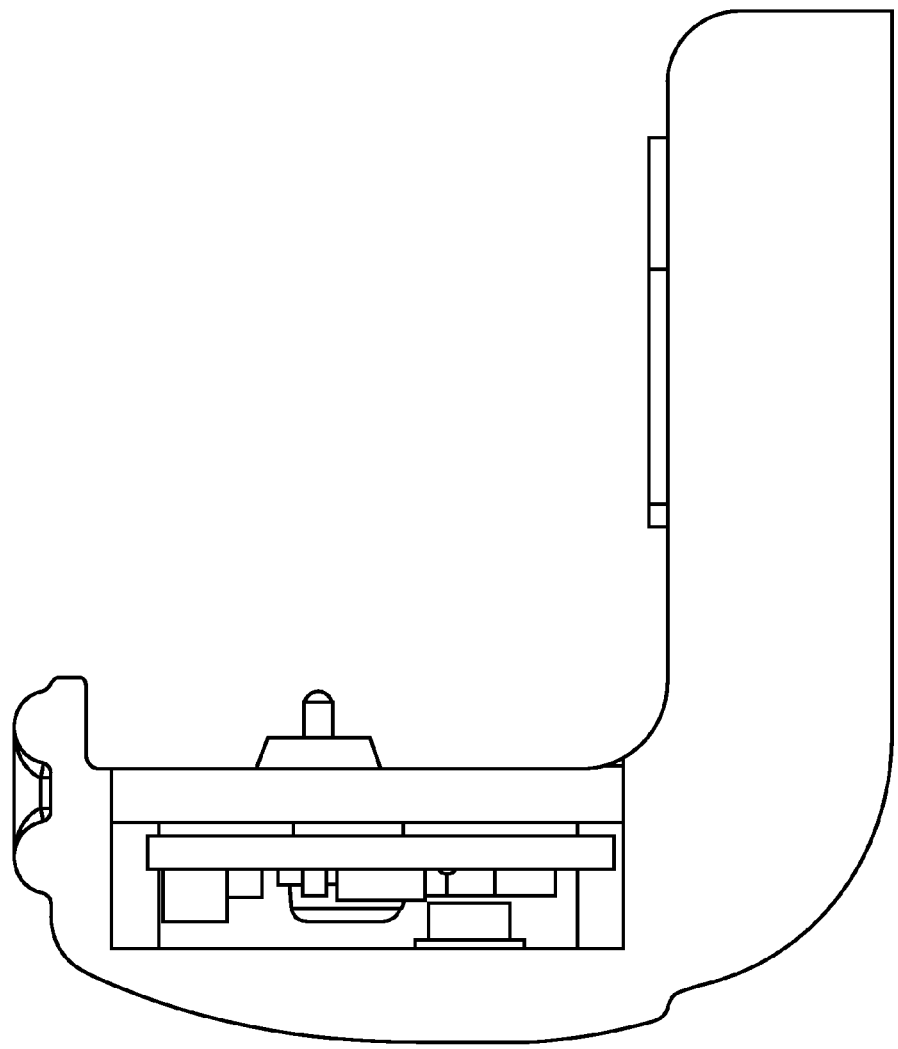
FIG. 35 is a projected view illustrating one embodiment of a power adapter having magnetic connections, and power connections.
Figure 36:
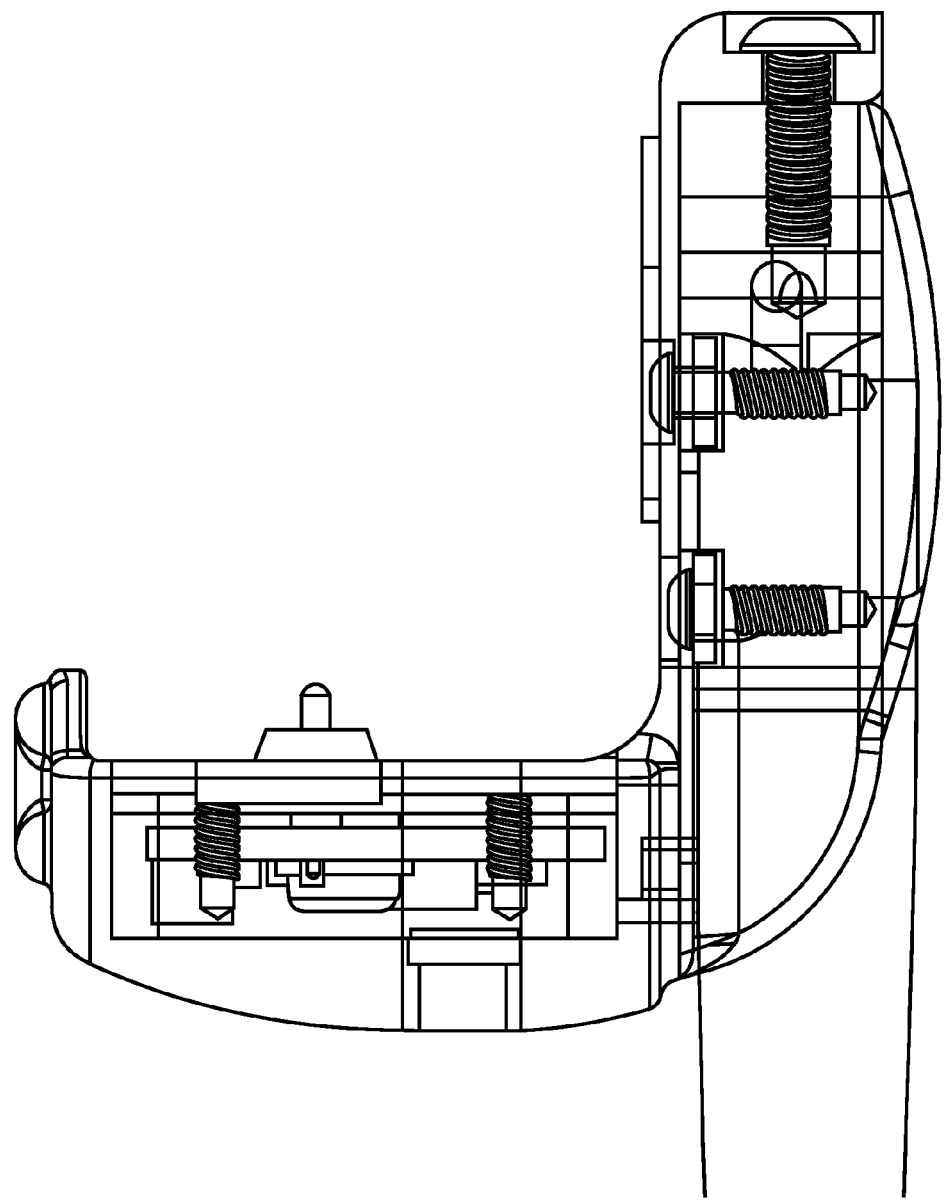
FIG. 36 is a projected view illustrating one embodiment of a power adapter having magnetic connections, and power connections.
Figure 37:
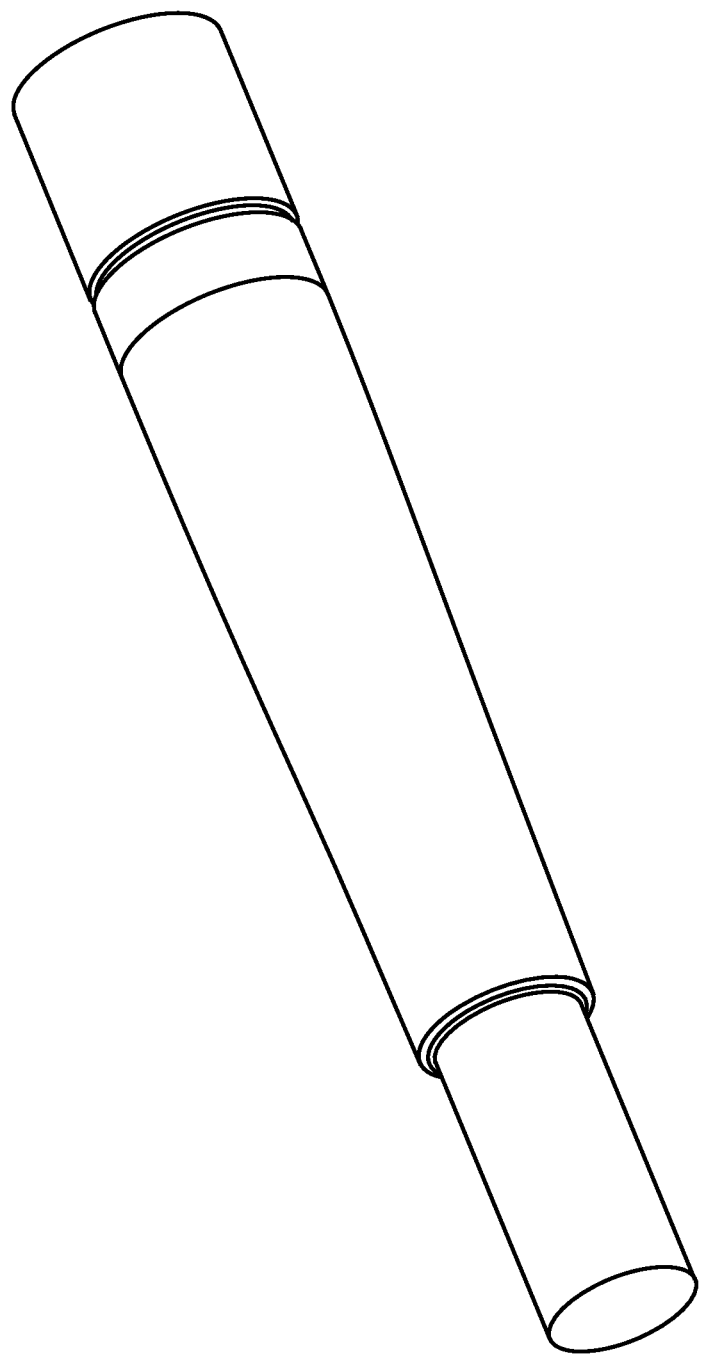
FIG. 37 is an perspective view illustrating one embodiment of a power adapter power cable housing.
Figure 38:
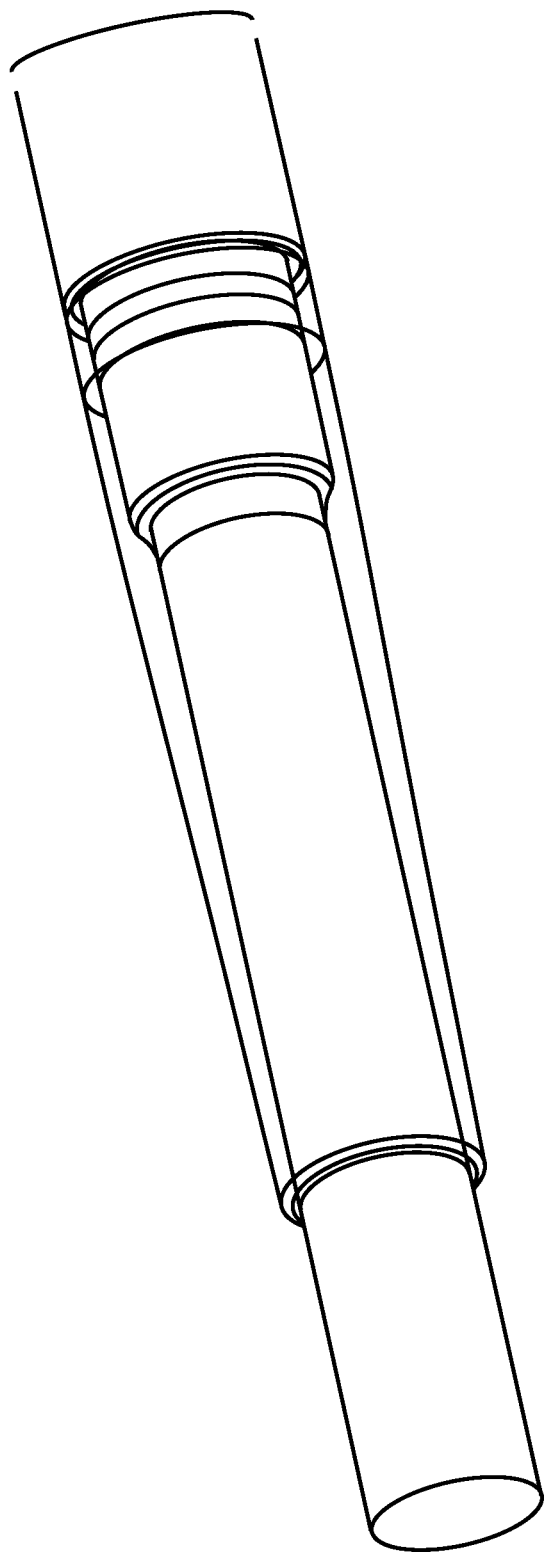
FIG. 38 is a partial perspective view illustrating one embodiment of a power adapter power cable housing.

FIGS. 9 through 38 illustrate various embodiments of the components discussed herein. Specifically, FIGS. 9 through 11 illustrate a system controller coupled to an external battery pack and percutaneous lead according to one embodiment. FIGS. 12 through 16 illustrate one embodiment of a system controller coupled to a power adapter and percutaneous lead. FIGS. 17 and 18 illustrate one embodiment of a system controller coupled to a percutaneous lead and decoupled from a power adapter. FIGS. 19 and 20 illustrate a power adapter according to one embodiment. FIGS. 21 through 26 illustrate one embodiment of a power adapter having magnetic connections and power connections. FIG. 27 is an exploded view illustrating one embodiment of a power adapter having magnetic connections and power connections. FIG. 28 is an exploded view illustrating a power adapter power cable, power connections, and magnets, according to one embodiment. FIG. 29 illustrates one embodiment of a power adapter power cable, power connections, and magnets. FIGS. 30 through 33 illustrate one embodiment of a power adapter power connection. FIGS. 34 through 36 illustrate a power adapter having magnetic connections and power connections, according to one embodiment. FIG. 37 is a perspective view illustrating one embodiment of a power adapter power cable housing. FIG. 38 is a partial perspective view illustrating one embodiment of a power adapter power cable housing.

Various embodiments and aspects of the inventions have been described above with reference to the accompanying drawings. The foregoing description and drawings are illustrative of the invention and are not to be construed as limiting the invention. Numerous specific details have been described to provide a thorough understanding of various embodiments of the present invention. However, in certain instances, well-known or conventional details have been omitted in order to provide a concise discussion of embodiments of the present inventions. It will be evident that various modifications may be made thereto without departing from the broader spirit and scope of the invention as set forth in the following claims.

Reference in the specification to one embodiment or an embodiment means that a particular feature, structure or characteristic described in connection with the embodiment is included in at least one embodiment of the invention. The appearance of the phrase "in one embodiment" in various places in the specification do not necessarily refer to the same embodiment.

An article of manufacture may be used to store program code providing at least some of the functionality of the embodiments described above. An article of manufacture that stores program code may be embodied as, but is not limited to, one or more machine readable non-transitory storage media such as memories (e.g., one or more flash memories, DRAM, random access memories—static, dynamic, or other), optical disks, CD-ROMs, DVD-ROMs, EPROMs, EEPROMs, magnetic or optical cards or other type of machine-readable non-transitory media suitable for storing electronic instructions. Additionally, embodiments of the invention may be implemented in, but not limited to, hardware or firmware utilizing an FPGA, ASIC, a processor, a computer, or a computer system including a network. Modules and components of hardware or software implementations can be divided or combined without significantly altering embodiments of the invention. The specification and drawings are, accordingly, to be regarded in an illustrative sense rather than a restrictive sense.

What is claimed is:

1. A system comprising:
   a battery comprising an integrated touchscreen;
   a first data connection port;
   a processing system coupled to the touchscreen and to the battery and to the first data connection port;
   a detachable device detachably coupled to the battery, the detachable device having a second data connection port adapted to be coupled to the first data connection port to send data from the detachable device to the processing system, the detachable device having a power port configured to receive power from the battery; and
   wherein the touchscreen is configured to provide a user interface to display on the touchscreen information based on the data received from the detachable device.

2. The system of claim 1 further comprising:
   a proximity sensor coupled to the processing system, the proximity sensor configured to determine when the detachable device is coupled to the battery.

3. The system of claim 2 wherein the proximity sensor is a magnetic switch.

4. The system of claim 2 wherein the proximity sensor causes the processing to attempt to exchange data between the first data connection port and the second data connection port in response to determining that the detachable device is coupled to the battery.

5. The system of claim 4 wherein the first data connection port and the second data connection port are coupled through an infrared communication link.

6. The system of claim 5 wherein the infrared communication link is initiated in response to the proximity sensor determining that the detachable device is coupled to the battery.

7. The system of claim 6 wherein the processing system is configured to cause power to be provided from the battery to the power port on the detachable device in response to successfully initiating the infrared communication link.

8. The system of claim 7 wherein the processing system is configured to send data to the detachable device through the infrared communication link.

9. The system of claim 8 wherein the processing system is configured to receive data from the detachable device through the infrared communication link.

10. The system of claim 9 wherein the detachable device further comprises an internal battery and the detachable device is configured to automatically switch to use the internal battery when the battery with the integrated touchscreen is detached from the detachable device.

11. The system of claim 10 wherein the detachable device is a system controller for a heart pump.

12. The system of claim 11 wherein the data received from the detachable device represents a status of the heart pump.

13. The system of claim 12 wherein the data received includes a status of the detachable device and the status includes one or more of alarm status, event history, pump parameters, log data, and power source status.

14. The system of claim 1 wherein the data received from the detachable device represents a status of a heart pump which is coupled to the detachable device.

15. The system of claim 1 wherein the detachable device is a system controller for a medical device.

16. The system of claim 1 wherein the data received includes one or more of: the status of the detachable device, an alarm status, event history, or power source status.

17. The system of claim 1 further comprising:
   a proximity sensor coupled to the processing system, the proximity sensor configured to determine when the detachable device is coupled to the battery; and wherein the data received from the detachable device represents a status of a heart pump which is coupled to the detachable device.

18. The system of claim 1 further comprising:
a proximity sensor coupled to the processing system, the proximity sensor configured to determine when the detachable device is coupled to the battery; and wherein the detachable device is a system controller for a medical device.

19. The system of claim 1 further comprising:
a proximity sensor coupled to the processing system, the proximity sensor configured to determine when the detachable device is coupled to the battery; and wherein the data received includes one or more of: the status of the detachable device, an alarm status, event history, or power source status.

20. The system of claim 1 wherein the detachable device further comprises an internal battery and the detachable device is configured to automatically switch to use the internal battery when the battery is detached from the detachable device.

21. The system of claim 1, wherein the detachable device further comprises an internal battery and the detachable device is configured to automatically switch to use the internal battery when the battery is detached from the detachable device and wherein the detachable device is a system controller for a medical device.

22. The system of claim 21, wherein the data received from the detachable device represents a status of the medical device, and wherein the medical device is coupled to the detachable device.

23. The system of claim 1, further comprising a housing, wherein the touchscreen is integrated onto a surface of the housing, and the housing contains the battery.

* * * * *